(12) United States Patent
Nakamura

(10) Patent No.: US 7,892,165 B2
(45) Date of Patent: Feb. 22, 2011

(54) CAMERA CALIBRATION FOR ENDOSCOPE NAVIGATION SYSTEM

(75) Inventor: Tetsuya Nakamura, Saitama-ken (JP)

(73) Assignee: Hoya Corporation, Tokyo (JP)

( * ) Notice: Subject to any disclaimer, the term of this patent is extended or adjusted under 35 U.S.C. 154(b) by 1065 days.

(21) Appl. No.: 11/551,927

(22) Filed: Oct. 23, 2006

(65) Prior Publication Data

US 2008/0097156 A1 Apr. 24, 2008

(51) Int. Cl.
*A61B 1/00* (2006.01)
*A61B 1/04* (2006.01)
(52) U.S. Cl. .................... 600/117; 600/109; 600/424
(58) Field of Classification Search ............ 600/109, 600/117, 424, 426, 427, 429, 473; 606/130; 73/1.79
See application file for complete search history.

(56) References Cited

U.S. PATENT DOCUMENTS

| | | | | |
|---|---|---|---|---|
| 6,272,371 | B1 * | 8/2001 | Shlomo | 600/424 |
| 6,490,475 | B1 * | 12/2002 | Seeley et al. | 600/426 |
| 6,511,418 | B2 * | 1/2003 | Shahidi et al. | 600/117 |
| 6,517,478 | B2 * | 2/2003 | Khadem | 600/117 |
| 6,846,286 | B2 | 1/2005 | Suzuki et al. | |
| 7,194,296 | B2 * | 3/2007 | Frantz et al. | 600/424 |
| 2004/0054489 | A1 * | 3/2004 | Moctezuma De La Barrera et al. | 702/105 |
| 2005/0288575 | A1 * | 12/2005 | de la Barrera et al. | 600/423 |
| 2006/0258938 | A1 * | 11/2006 | Hoffman et al. | 600/424 |
| 2008/0091069 | A1 * | 4/2008 | Groszmann | 600/117 |

FOREIGN PATENT DOCUMENTS

JP 2001-187067 7/2001

OTHER PUBLICATIONS

English language abstract of JP 2001-187067.
Yamaguchi et al., "Development of a camera model and calibration procedure for oblique-viewing endoscopes", Computer Aided Surgery, 2004; 9(5): 203-214, URL:http://www.image.med.osaka-u.ac.jp/member/yoshi/paper/YamaguchiCA2004.pdf.
"Graduate School of Information Science, Nagoya University, Web News", URL:http://www.is.nagoya-u.ac.jp/v2n1_0301.html, retrieved on Sep. 11, 2006 and English translation thereof.
"Tsai CameraCalibration",URL:http://homepages.inf.ed.ac.uk/rbf/CVonline/LOCAL_COPIES/DIASI/,retrieved on Sep. 11, 2006.
"Camera Calibration Toolbox for Matlab", URL:http://www.vision.caltech.edu/bouguetj/calib_doc/, retrieved on Sep. 11, 2006.
"Medical & Medical Simulation", URL:http://www.ascension-tech.com/applications/medical.php, retrieved on Jan. 23, 2007.

(Continued)

*Primary Examiner*—John P Leubecker
*Assistant Examiner*—Jeffrey H Chang
(74) *Attorney, Agent, or Firm*—Greenblum & Bernstein, P.L.C.

(57) ABSTRACT

A scope navigation apparatus, method and a program embodied computer readable medium for navigating a scope end that is to be inserted into an object. The scope end includes at least one sensor that senses a spatial location of the scope end. An image pickup device records one or more images of a calibration device, which includes a sensor that senses a location of the calibration device. A processor calibrates the images recorded by the image pickup device and corrects for intrinsic and extrinsic parameters using a calibration matrix.

20 Claims, 16 Drawing Sheets

OTHER PUBLICATIONS

Christian Wengert et al, "Markerless Endoscopic Registration And Referencing", URL:http://www.vision.ee.ethz.ch/publication/pub readall.cgi?lang=en&authors=Wengert.

Christian Wengert et al, "Fully Automatic Endoscope Calibration for Intraoperative Use", URL:http://www.vision.ee.ethz.ch/publication/pub readall.cgi?lang=en&authors=Wengert.

Gerald Bianchi et al, "Camera-Marker Alignment Framework and Comparison with Hand-Eye Calibration for Augmented Reality Applications", URL:http://www.vision.ee.ethz.ch/publication/pub readall.cgi?lang=en&authors=Wengert.

"Yoshinobu Sato, Ph.D.," URL:http://www.image.med.osaka-u.ac.jp/member/yoshi/index.html, retrieved on Jan. 23, 2007.

Michael Figl et al, A Fully Automated Calibration Method for an Optical See-Through Head-Mounted Operating Microscope With Variable Zoom and Focus; IEEE Transactions on Medical Imaging, vol. 24, No. 11, Nov. 2005 1492-1499.

Yoshinobu Sato et al, Image Guidance of Breast Cancer Surgery Using 3-D Ultrasound Images and Augmented Reality Visualization, IEEE Transactions on Medical Imaging, vol. 17, No. 5, Oct. 1998 681-693.

* cited by examiner

Fiberscope

Sensor coil

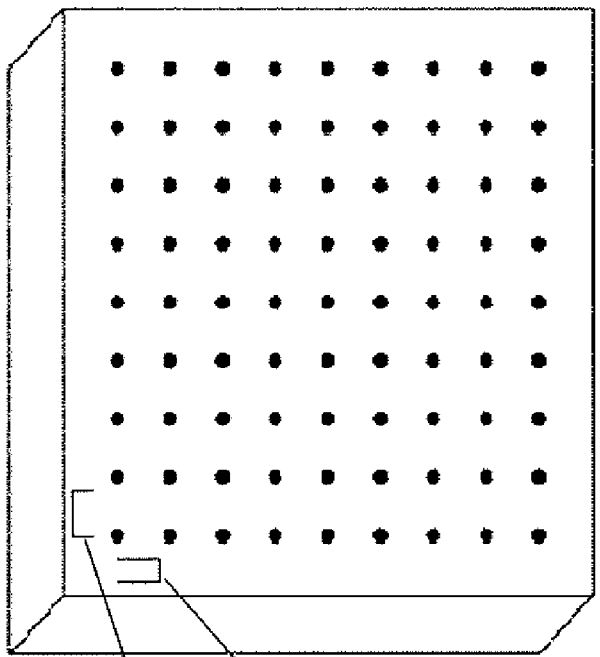
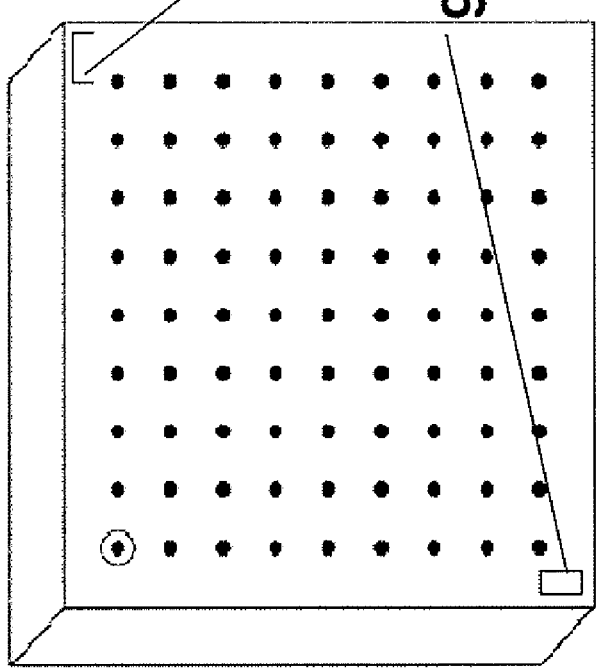

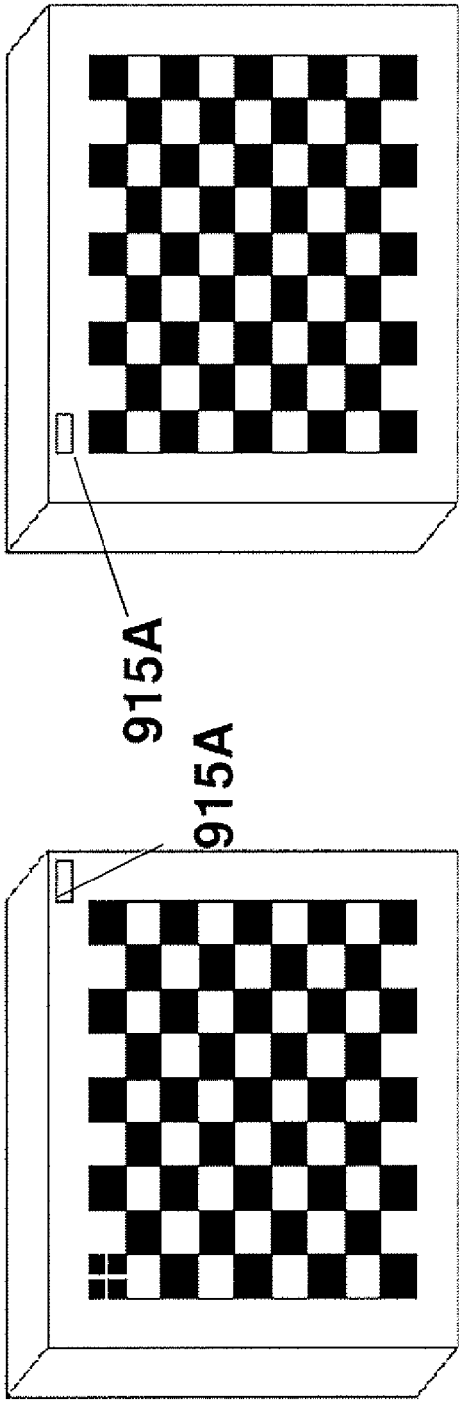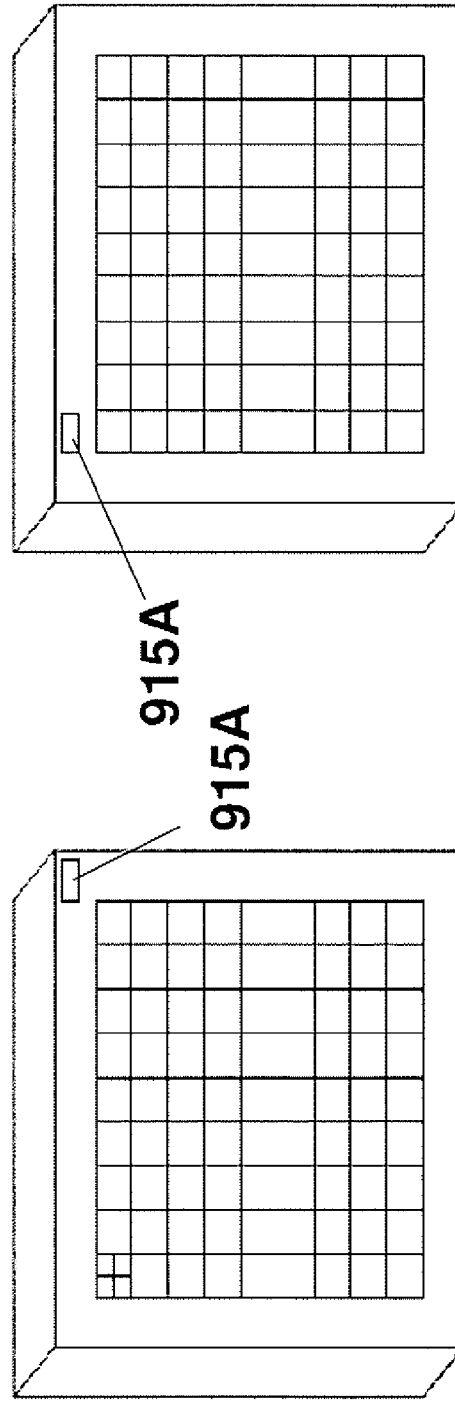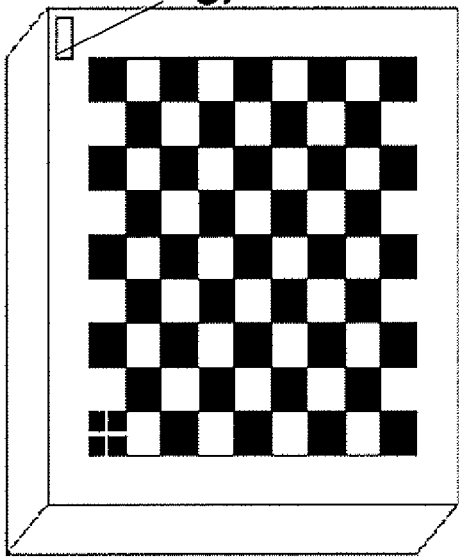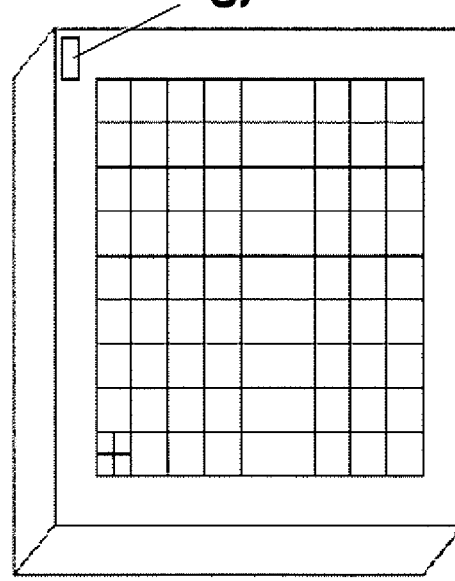

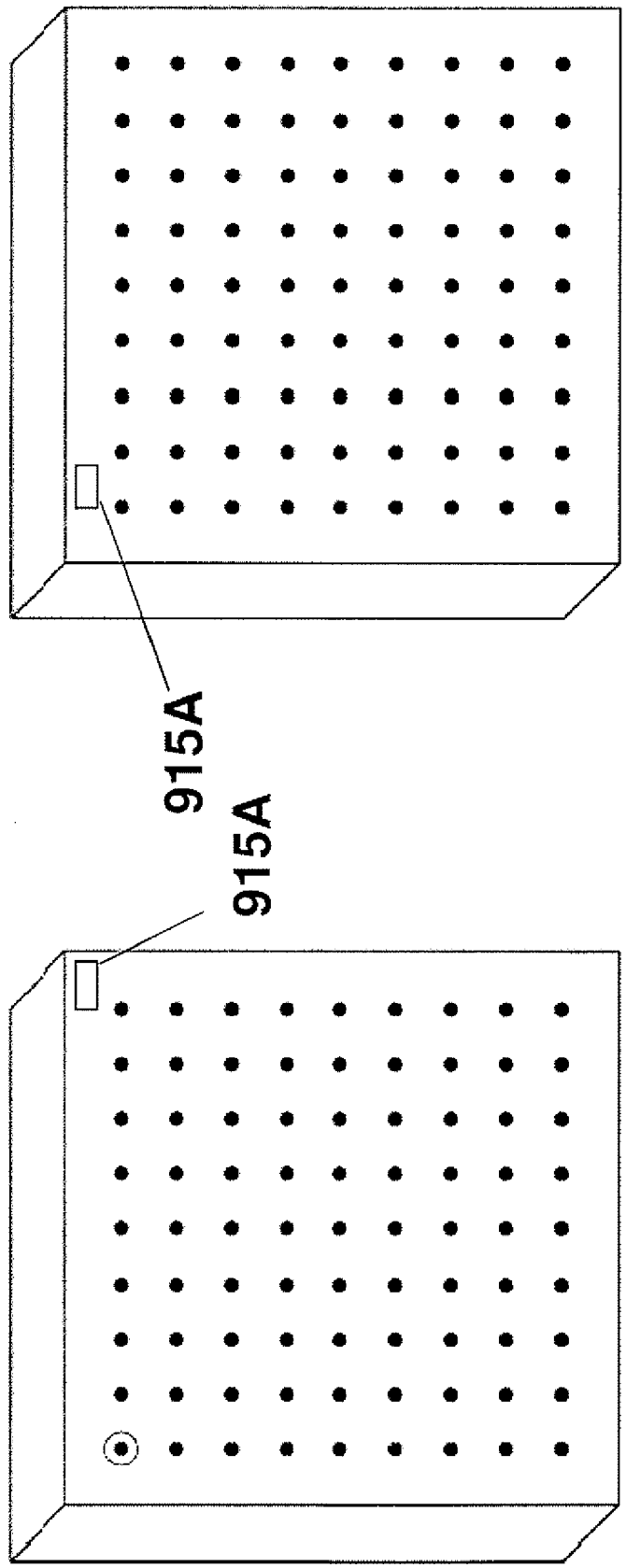

CAMERA CALIBRATION FOR ENDOSCOPE NAVIGATION SYSTEM

BACKGROUND OF THE DISCLOSURE

1. Field of the Disclosure

The present disclosure relates to a scope navigation system and an image pickup calibration system for a scope navigation system. More particularly, the present disclosure relates to an apparatus, method and computer code product for accurately navigating a scope and calibrating an image pickup device for a scope navigation system.

2. Background of the Disclosure

Minimally-invasive medical procedures have become commonplace with imaging systems that allow users, such as for example, clinicians, researchers and others to see inside bodies of living organisms with amazing clarity. Users are turning to endoscopes, which is one type of scope, as a first line tool in researching, evaluating, diagnosing and/or performing medical procedures where minimal invasive intrusion is desired and/or necessary.

Endoscopes have become prevalent throughout the scientific community, with the greatest proliferation occurring in setting such as, for example, clinics, operating rooms, doctor offices, and the like. Part of the reason for the ubiquitousness of endoscopes has been because they facilitate minimally-invasive diagnostic and surgical medical procedures. Endoscopes are typically used to evaluate interior surfaces of, for example, the human body. Typically, endoscopes may be retrofitted with diagnostic and/or surgical instruments that may be remotely operated by a user.

Contemporary endoscopes may be categorized into at least two groups, including, for example, rigid endoscopes and flexible endoscopes. A typical endoscope, whether it is a rigid or flexible endoscope, includes a light delivery system to illuminate an object under inspection, such as, for example, an organ; a lens, or lens system, for projecting an image of the object; an image pickup device, such as, for example, a charge coupled device (CCOD), for recording the projected image of the object under inspection; a processor that receives image signals from the image pickup device and converts the image signals to humanly perceivable display images; and a display that displays the perceivable images.

The contemporary rigid endoscope differs from its flexible counterpart in that it uses a rigid insertion portion and transmits an image through a lens system. Typically, an optical sensor is attached to a handle in a rigid endoscope. Whereas the flexible endoscope uses a flexible insertion portion and typically transmits an image through a flexible system, such as, for example, a fiberscope. Generally, an optical sensor is placed into a distal end portion of a flexible endoscope.

As the popularity of endoscopes has grown and become commonplace in medical procedures, the complexity of the hardware and software equipment that accompanies the endoscopes has also grown. Particularly, as the quality and clarity of the picked-up images has improved, users have learned to depend on the endoscopes more than ever in accurately performing medical diagnostic and/or surgical procedures. As a result, various methodologies have been developed to correct for system imperfections pertaining to, for example, video cameras and their implementations at the micro-level, as well as the interplay between the various coordinate systems.

Three commonly used camera calibration methods are the Direct Linear Transform (DLT), R. Y. Tsai, and Z. Zhang methods. Of the three, Tsai's method is the oldest and most widely used in computer vision systems because of its effective and noteworthy performance. There are numerous implementations of the Tsai calibration method using C, C++ and other high-level computer languages. The Tsai method has been used to correct for internal camera geometric and optical characteristic imperfections (intrinsic parameters) and/or errors resulting due to the three dimensional position and orientation of the camera frame relative to a certain world coordinate system (extrinsic parameters).

Scope systems that use camera calibration and take into consideration the various coordinate systems in aiding a user in navigating the scope are sometimes referred to as augmented reality (AR) systems. AR systems are typically display-based in that the final image displayed to the scope operator is accurately depicted in terms of both its positional aspect and its time aspect.

In order to facilitate hand-eye coordination by the scope operator, display-based AR technologies have been mated to three-dimensional (3D) position sensor scope tracking technology, allowing users to accurately track movements of the endoscope while viewing a displayed image of the area sensed by the scope. However, a significant limitation of scopes remains, including AR-based endoscopes. Namely, the coordinate system of the image picked up by a scope has an imprecise relationship to the coordinate system perceived by the operator, such as, for example, the hand-eye coordination between the scope as manipulated by the user and the image displayed on the external monitor to the user.

Japanese Patent Application Publication No. 2001-187067 describes an AR-based endoscope that compensates for the various coordinate systems existing in an endoscope observation system. As illustrated in FIG. 1, Publication No. 2001-187067 describes an endoscope observation position detecting and indicating system that allows a user to accurately navigate an endoscope in real time while viewing a corresponding image that is picked up by the endoscope. The known navigation system detects the observation position of an endoscope 1. The system employs a calculation device 7 to compute the endoscope observation position by processing signals received from an optical detector 8, via signal line 9, and a sensor arm 5, via signal line 6, to detect an observation position of the endoscope 1. A monitor 10 displays an image picked up by a video camera 4. The video camera 4 and sensor arm 5 are supported by support arm 2 and guide 3. Thus, by using, for example, detector 8, and an optical sensor attached to video camera 4, the known system is able to track the position of the camera. However, the optical navigation system shown in FIG. 1, which employs an optical sensor attached to the handle, does not work for a flexible endoscope, whose distal end portion is curved.

In flexible scopes it has been a practice to insert a magnetic sensor, for example, through a scope forceps channel, or to build the sensor into a distal end portion of a scope as shown, for example, in FIG. 2. However, the offset between an optical axis of the scope and the central axis of the sensor creates a misalignment between the actual image picked up by the scope and the location of the image as sensed by the sensor.

SUMMARY OF THE DISCLOSURE

It as a feature of the invention to provide an accurate three dimensional relationship between a calibration device and a picked-up scope image.

According to an aspect of the invention, a scope navigation apparatus is provided. The scope navigation apparatus includes a scope that is to be inserted into an object. The scope includes one or more image pickup devices and one or more sensors, wherein the one or more sensors include a central axis that is offset from an optical axis of the one or more image pickup devices. The one or more sensors may be inserted into a channel of the scope, or affixed to the scope, or made into part of the scope.

The apparatus also includes a calibration device and one or more calibration device sensors positioned in a fixed position in relation to the calibration device. The one or more image pickup devices record at least one image of the calibration device. A location determiner is provided that senses a location of the one or more sensors and a location of the one or more calibration device sensors. The location determiner may include a sensor interface unit and a system control unit, wherein the sensor interface unit senses the location of the one or more sensors and the location of the one or more calibration device sensors. A field generator is provided that generates an electromagnetic field, wherein the location determiner senses the location of the at least one sensor and the location of the one or more calibration device sensors based on the electromagnetic field. The calibration device may be positioned in a fixed relation to the field generator. Further, the calibration device may be at least one of a checkerboard pattern, a dot pattern, or a grid pattern.

The apparatus further includes a processor that corrects the at least one image recorded by the one or more image pick up devices based upon the location of the one or more sensors and the location of the one or more calibration device sensors. A video processor is provided that processes the video signals output by the one or more image pickup devices. A host device is provided that may process (in addition to the video processor or instead of the video processor) the video signals output by the one or more image pickup devices. The host device and/or the video processor correct the at least one image recorded by the one or more image pickup devices.

According to another aspect of the invention, a method is provided for calibrating and correcting an image to be displayed. The method includes a process of recording an image of a calibration device, where the calibration device is located in a fixed position in relation to at least one calibration device sensor. A further process of determining an optical axis of an image pickup device is provided, where the image pickup device includes at least one sensor. A further process is provided for detecting a location of the at the least one calibration device sensor and a location of the at least one other sensor. A process is provided for determining a parameter value for calibrating the image pickup device.

The process for determining a parameter value includes a process for selecting a first point on the recorded image and a process for calculating a first determination point based on the selected first point. The determining process also includes a process for determining a difference value between the selected point and the first determination point, and a process for comparing the difference value with a threshold value. A process is provided for determining the difference value to be greater than, or equal to the threshold value. And, a process is provided for calculating a calibration matrix for calibrating the image pickup device. The parameter value determining process may include a process for setting the first point as an origin point and selecting a second point in at least one of a clockwise and counterclockwise direction.

Further, a process is provided for compensating an offset between a central axis of the at least one sensor and the optical axis of the image pickup device. A process is provided for calibrating the recorded image based on the parameter value. The calibrating process may be based on five degrees of freedom, six degrees of freedom, or a combination of both. The calibration matrix may have at least one intrinsic parameter and at least one extrinsic parameter. Further, the calibration matrix may be based on a relationship between a three dimensional coordinate system of the calibration device and a two dimensional coordinate system of the image pickup device.

According to another aspect of the invention a computer readable medium is provided that includes an image recording code segment that causes recording an image of a calibration device, the calibration device located in a fixed position in relation to at least one sensor. The medium includes a determining code segment that causes determining an optical axis of an image pickup device, the image pickup device including at least one other sensor. The medium includes a detecting code segment that causes detecting a location of the at the least one sensor and a location of the at least one other sensor. Further, the medium includes a parameter determining code segment that causes determining a parameter value for calibrating the image pickup device. Further, the medium includes a compensating code segment that causes compensating an offset between a central axis of the at least one other sensor and the optical axis of the image pickup device. Further, the medium includes a calibrating code segment that causes calibrating the image pickup device based on the parameter value.

The determining code segment may be provided with a point selecting code segment that causes selecting a first point on the recorded image, a determination point calculating code segment that causes calculating a first determination point based on the selected first point, a difference value determining code segment that causes determining a value between the selected point and the first determination point, and a difference value comparing code segment that causes comparing the difference value with a threshold value.

The computer readable medium may include a difference value determining code segment that causes determining the difference value to be greater than, or equal to the threshold value, and a calibration matrix code segment that causes calculating a calibration matrix for calibrating the image pickup device. The calibrating may be based on at least one of five degrees of freedom and six degrees of freedom, and wherein the calibration matrix includes at least one intrinsic parameter and at least one extrinsic parameter. Further, the calibration matrix may be based on a relationship between a three dimensional coordinate system of the calibration device and a two dimensional coordinate system of the image pickup device.

Other exemplary embodiments and advantages of the present invention may be ascertained by reviewing the present disclosure and the accompanying drawings; and the above description should not be considered to limit the scope of the present disclosure.

BRIEF DESCRIPTION OF THE DRAWINGS

The present disclosure is further described in the detailed description that follows, by reference to the noted drawings by way of non-limiting examples of embodiments of the present disclosure, in which like reference numerals represent similar parts throughout the several views of the drawings:

FIGS. 11A-11B are illustrations of alternative examples of calibration devices with two sensors that may be used according to an aspect of the invention;

FIGS. 12A-12D are illustrations of examples of calibration devices with a single sensor that may be used according to an aspect of the invention;

FIGS. 13A-13B are illustrations of alternative examples of calibration devices with a single sensor that may be used according to an aspect of the invention;

DETAILED DESCRIPTION OF THE DISCLOSURE

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodiment in practice.

According to the Tsai method, cameras may be calibrated so as to correct for distortions resulting from, for example, internal camera geometric and optical characteristics (intrinsic parameters) and/or the three dimensional position and orientation of the camera frame relative to a certain world coordinate system (extrinsic parameters). Intrinsic parameters typically pertain to a relationship between a set of camera-centered coordinates and a set of image-centered coordinates. Extrinsic parameters, which pertain to an external orientation between the camera and its surrounding environment, are determined as the relationship between the surrounding environment coordinate system and the camera coordinate system.

Figure 1:
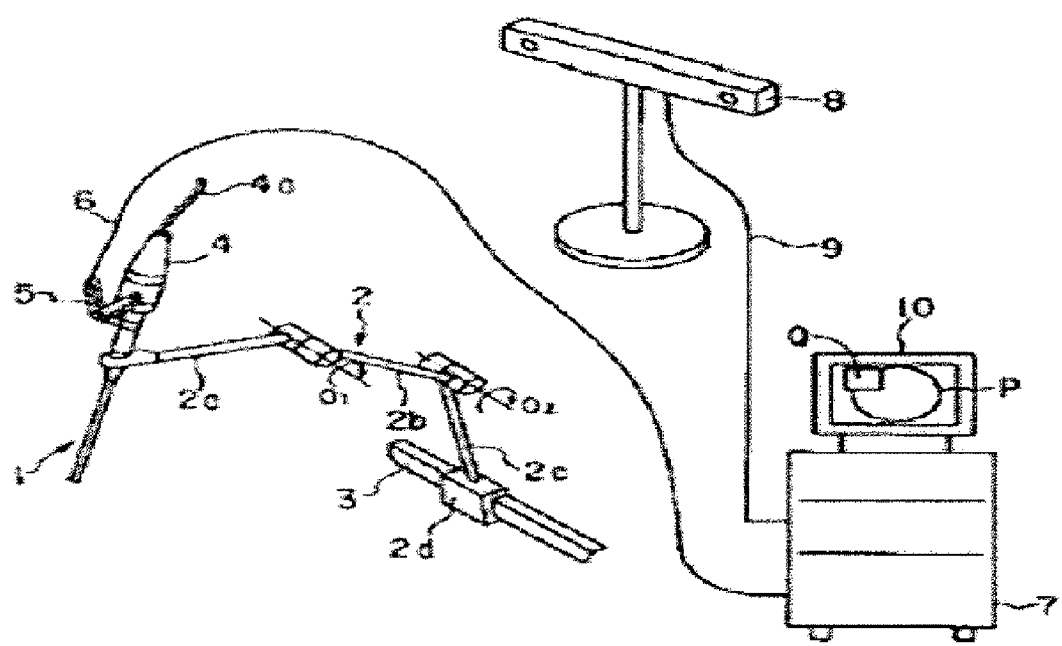
FIG. 1 is an illustration of a known rigid endoscope navigation system.
Figure 2:
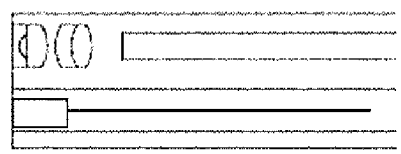
FIG. 2 is an illustration of a fiberscope end that may be used according to an aspect of the invention.
Figure 3:
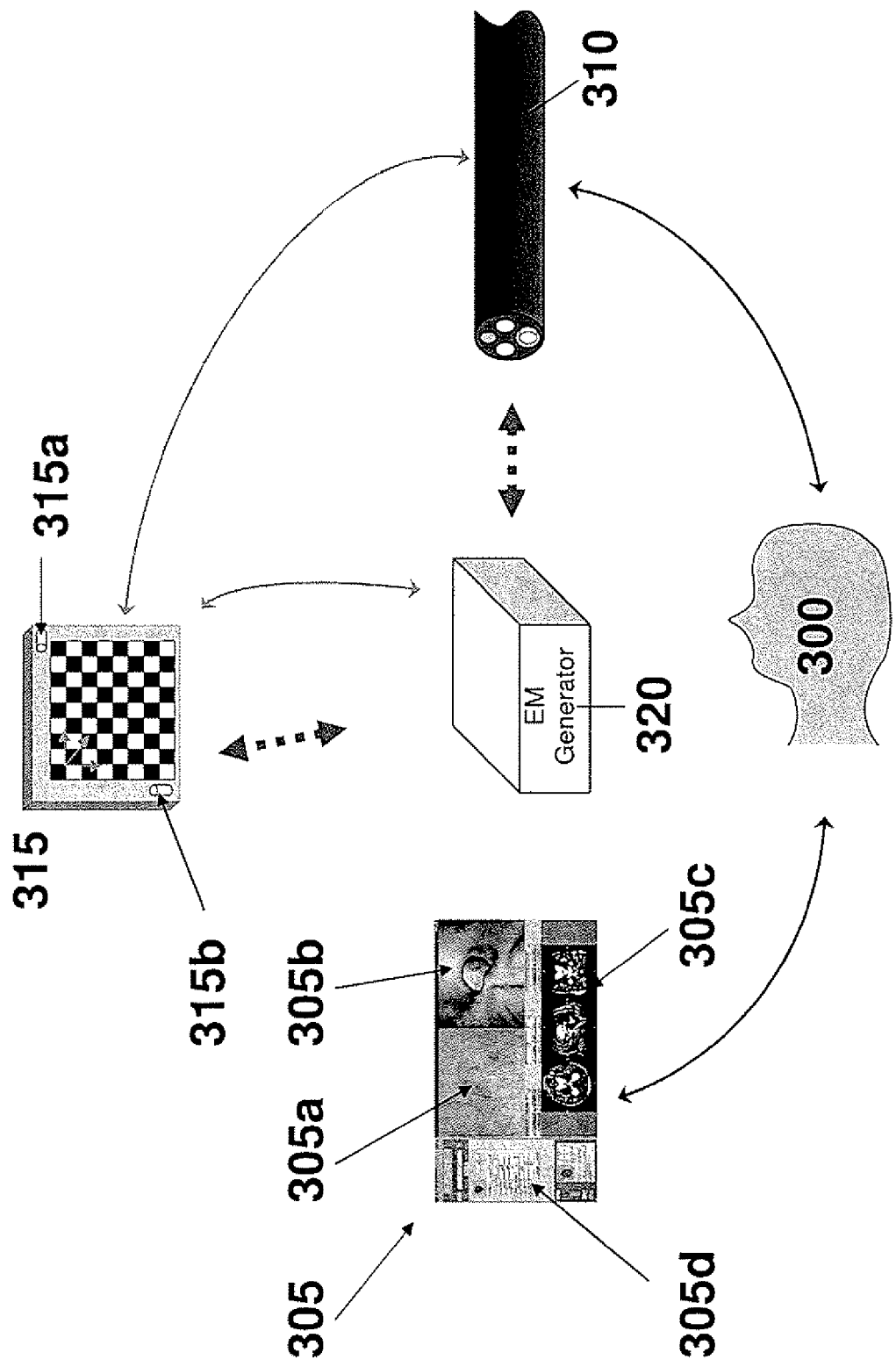
FIG. 3 is an illustration of endoscope navigation system according to an aspect of the invention.

In the exemplary embodiment shown in FIG. 3, a patient 300, who is to undergo a procedure, such as, for example, a neuroendoscopic procedure, is placed on a fixed surface such as, for example, a surgical table in an operating room. The patient may be positioned in any position appropriate for the type of procedure that is to be performed, including, for example, but not limited to, a supine position, a prone position, a decubitus position, etc. A Computed Tomographic (CT) image, commonly known as CT scan (also known as a Computed Axial Tomography (CAT) scan) is taken of an area of the patient (in this example, the patient's head) and recorded prior to the intended procedure. A display 305, including display areas 305a, 305b, 305c and 305d, is provided to convey necessary images to a user. The previously recorded CT image, or model image is displayed on a display area 305a along side a real-time image 305b that is picked up by an endoscope 310. A graphic user interface area 305d is provided for enabling a user to easily control system parameters such as, for example, light intensity, image processing, and the like. Display area 305c is provided for displaying, for example, a general tomographic map of an area of the patient that is to undergo a procedure. In the illustration of FIG. 3, an exemplary CT image of the patient's brain is shown.

Although the model image 305a is generated from a CT scan, a magnetic resonance image (MRI), a Tomographic image (such as, for example, Linear Tomography, Poly Tomography, Zonography, or Orthopantomography), or an ultrasound image, or the like, may equally be used. The displayed model image is displayed as is well known in the art for displaying medical images.

Moreover, the display 305 may be any display device capable of generating a humanly perceivable image, such as, for example, but not limited to, a projection display device, holographic display, micromirror display, plasma display (PDP), cathode ray tube display (CRT), light emitting diode display (LED), organic light emitting diode display (OLED), surface-conduction electron-emitting display (SED), carbon-nanotube, nanocrystal display, or the like, without departing from the spirit and/or scope of the invention. Moreover, the display housing is not limited to a stationary device, but may be a portable device, such as a display device that may be attachable to a user via a head mount display system, or a projection device that projects a high-definition image of the preprocedure image on to the area of the patient that is intended to undergo the procedure, or on a half-mirror placed between the patient and the clinician, accurately superimposing the image so that the operator can readily and easily perceive the underlying area by viewing the superimposed projected image on the patient's area.

The exemplary endoscope 310 is a flexible endoscope whose distal end portion may be curved when maneuvering through the human body. U.S. Pat. No. 6,846,286 to Naoki Suzuki et al, which issued on Jan. 25, 2005, describes a flexible endoscope that may be used in an embodiment according to an aspect of the invention. U.S. Pat. No. 6,846,286 to Suzuki et al., is hereby incorporated in its entirety by reference. The endoscope tip shown in FIG. 3, which is also shown in larger scale in FIG. 6, includes an optical system, at least one sensor, and a light projection system. The endoscope is initially calibrated by positioning the endoscope so that a checkerboard pattern 315 is within the optical field of view of the endoscope's image pickup system. The device 315, containing the checkerboard pattern, includes two electromagnetic markers 315a and 315b. One or more image frames of the checkerboard pattern are picked by endoscope 310 image pickup system and used to calibrate the image pickup device.

Then, using the Tsai calibration method via, for example, a MATLAB® toolbox, the endoscope is calibrated.

Although the preferred embodiment of the invention is described as using a MATLAB® toolbox to execute the Tsai calibration algorithms, the skilled artisan will readily appreciate that any other software toolbox may be used and mated in to any calibration method, or combination thereof, including, for example, Direct Linear Transform (DLT), Z. Zhang, or any other method that is capable of effectively and accurately calibrating an image pickup system. Moreover, the software toolbox may include any other high-level computer programming language instead of MATLAB® that is capable of effectively executing the necessary calibration algorithms, such as, for example, but not limited to, Java, C/C++, Object Pascal, Perl, or any other language capable of carrying out an aspect of the invention without departing from the spirit and/or scope of the invention.

Positional information of the endoscope tip is sensed by an Electromagnetic (EM) generator 320 that senses the three-dimensional location of the sensor built into the tip. The EM generator 320 is an integrated electromagnetic tracking system such as, for example, an NDI AURORA® Electromagnetic Tracking System (manufactured by Northern Digital, Inc.) or a MicroBIRD™ Tracking System (manufactured by Ascension Technology Corp.). However, the skilled artisan will readily appreciate that any other non-optical tracking system capable of accurate position determination may be equally used without departing from the spirit and/or scope of the invention.

Figure 4:
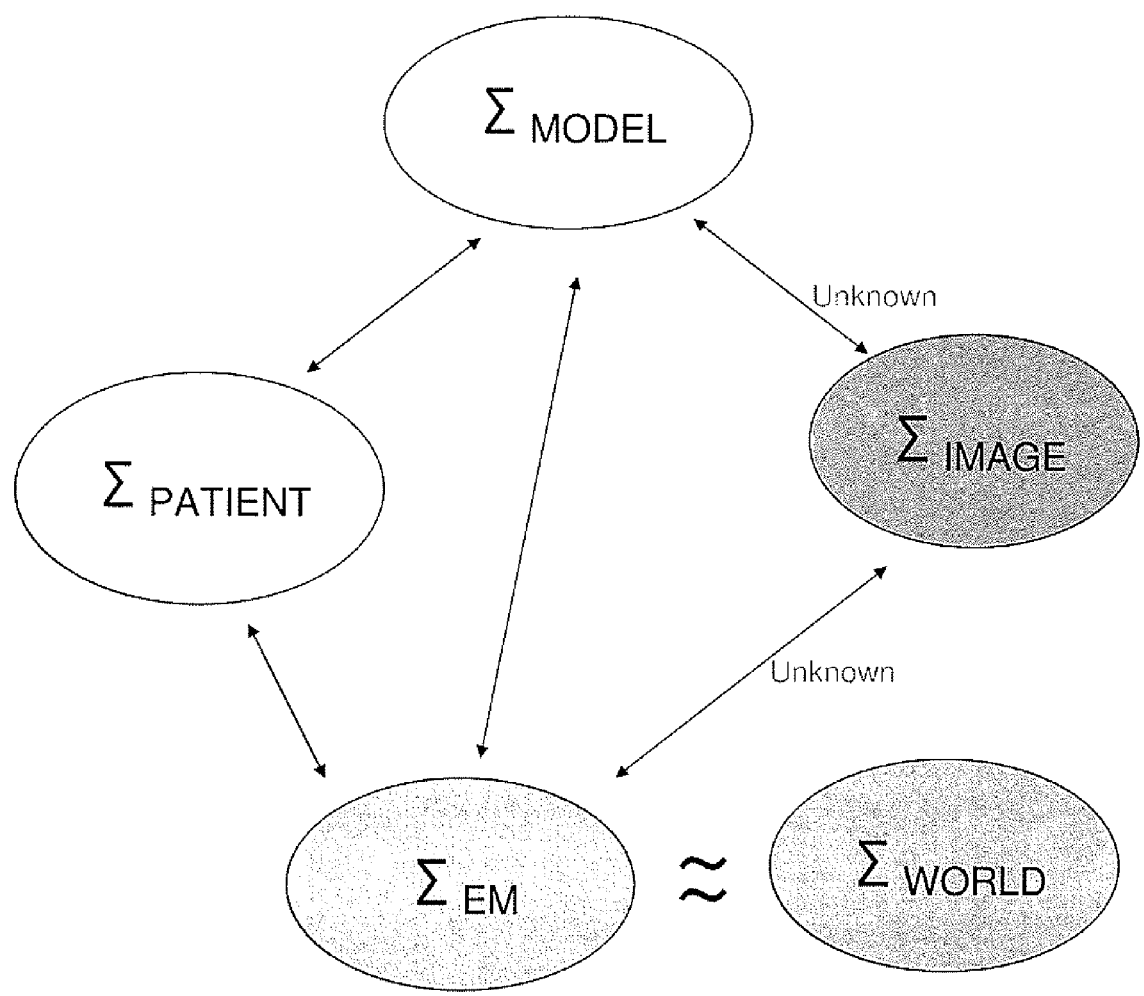
FIG. 4 is a diagram of the coordinate systems that are taken into consideration for the elements of FIG. 3 according to an aspect of the invention.

As shown in FIG. 4, the CT scan model image that is displayed on display 305 possesses, for example, spatial coordinates of a $\Sigma_{MODEL}$ ($x_{MODEL}$, $y_{MODEL}$, $z_{MODEL}$) coordinate system (hereinafter, the symbol "$\Sigma$" represents an n-dimensional coordinate system, where n is an integer greater than, or equal to 0). The patient 300 is positioned on, for example, a horizontal surface in a decubitus position and has spatial coordinates in coordinate system $\Sigma_{PATIENT}$ ($x_{PATIENT}$, $y_{PATIENT}$, $z_{PATIENT}$). The EM generator 320 has spatial coordinates in coordinate system $\Sigma_{EM}$ ($x_{EM}$, $y_{EM}$, $z_{EM}$). The image picked up by the endoscope has coordinates in the coordinate system $\Sigma_{IMAGE}$ ($x_{IMAGE}$, $y_{IMAGE}$). As shown by the arrows in FIG. 4, the relationships between the coordinate systems $\Sigma_{MODEL}$, $\Sigma_{PATIENT}$ and $\Sigma_{EM}$ are readily determinable by conventional methods. However, the relationships between the $\Sigma_{IMAGE}$ coordinate system and either of coordinate systems $\Sigma_{MODEL}$ and $\Sigma_{EM}$ is not known and must be accurately determined. For the purposes of simplifying the explanation of the exemplary embodiment, it may be assumed that the $\Sigma_{EM}$ coordinate system represents the real world coordinate System, $\Sigma_{WORLD}$, that the user of the endoscope 310 will perceive (such as, for example, through hand-eye coordination) as the operator manipulates the endoscope device.

Figure 5:
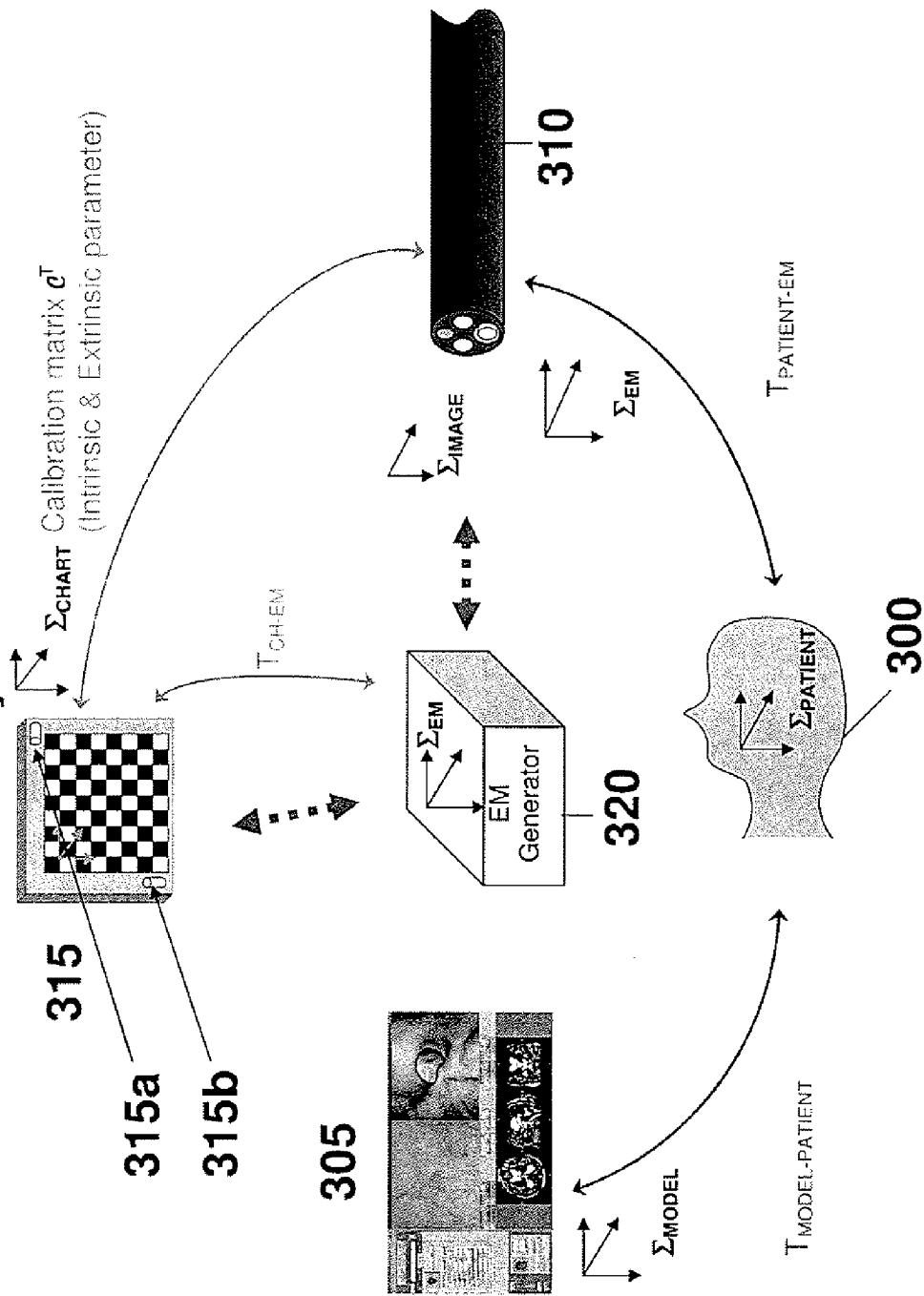
FIG. 5 is a more detailed representation of the illustration of FIG. 3, including the coordinate systems that are taken into consideration.

FIG. 5 shows the exemplary embodiment of FIG. 3 with the various coordinate systems shown, including the necessary transformations that are performed in order to accurately calibrate the scope system As shown in FIG. 5, the checkerboard pattern has a three-dimensional coordinate system $\Sigma_{CHART}$. In order to properly register the coordinate system of the image picked up by the endoscope ($\Sigma_{IMAGE}$) with the chart coordinate system ($\Sigma_{CHART}$), the image coordinate system is calibrated using a calibration matrix $\mathcal{C}^T$, which includes both intrinsic and extrinsic calibration parameters, as described below. The matrix $\mathcal{C}^T$ defines the relationship between the coordinate system of the chart and the coordinate system of the image sensed by the endoscope.

Figure 6:
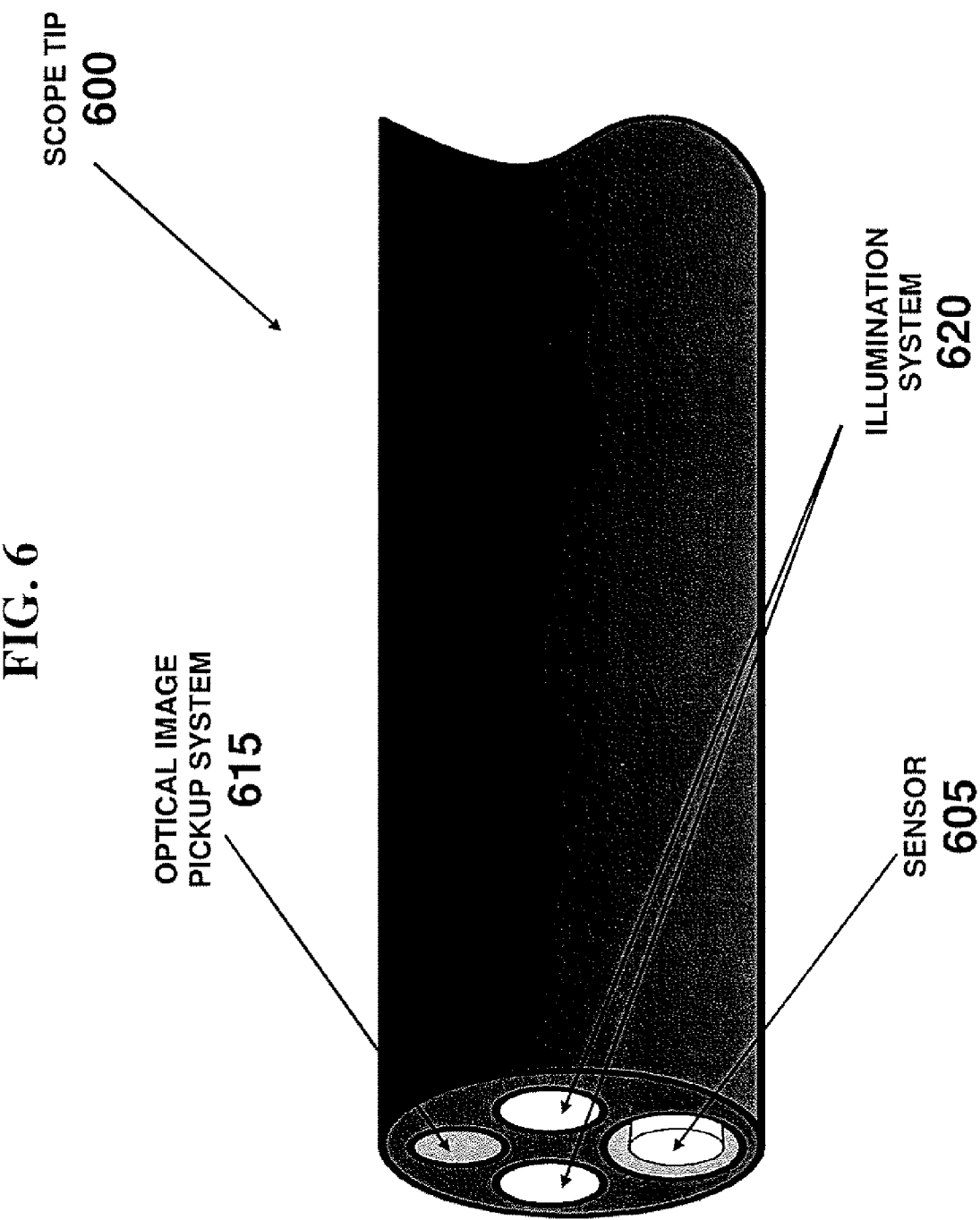
FIG. 6 is an example of an endoscope end that maybe used according to an aspect of the invention.

Referring to FIG. 6, the endoscope tip 600 includes EM sensor 605, optical image pickup system 615, and illumination system 620. The EM generator 320 (shown in FIG. 5) senses the position of the sensor 605 and determines the spatial coordinate system of the scope tip 600 The scope tip 600, which operates in the real world coordinate system ($\Sigma_{WORLD}$) has the coordinate system $\Sigma_{WORLD}$, which is substantially equal to the EM coordinate system ($\Sigma_{EM}$), as sensed by the EM generator 320. As illustrated in FIG. 6, the sensor 605 is offset from the optical axis of the image pickup system 615. This positional offset of the sensor from the optical axis of the image pickup system introduces both intrinsic and extrinsic errors that are corrected according to a non-limiting aspect of the invention described below.

Although the position sensor has been described using at least one EM sensor, other types of sensor systems may be used to detect the position of the scope tip and/or scope tube, such as, for example, ultrasound sensors, infrared sensors, or the like, without departing from the scope and/or spirit of the invention.

As shown in FIG. 5, the relationship between the patient's coordinate system ($\Sigma_{PATIENT}$) and the EM coordinate system ($\Sigma_{EM}$), including the spatial coordinates of the sensor 605 (shown in FIG. 6) is determined, and is represented by the transform matrix $T_{PATIENT-EM}$. The relationship $T_{PATIENT-EM}$ may be determined by any one of a number of different methods. For example, the relationship may be determined by having the user, using the scope tip 600, briefly touch the patient on an area where the procedure is to be performed. For example, the user would briefly touch a number of conical skin fiducials in order to get an accurate reading. The EM generator would record the positions at which the patient is touched, including the corresponding coordinate system ($\Sigma_{PATIENT}$).

Alternatively, or in addition to the multiple skin fiducial registration process described above, a number of electromagnetic tracking (marker) sensors may be affixed to the patient. The tracking sensors provide continuous and real time patient positioning information to the EM generator 320, allowing the EM generator to accurately sense the coordinates of the patient ($\Sigma_{PATIENT}$) even when the patient moves. Other patient registration methodologies may be employed, e.g., depending on the type of procedure that is to be performed, the patient's position during the procedure, whether the patient is to remain awake during the procedure, or the like, as the skilled artisan will readily appreciate without departing from the scope and/or spirit of the invention.

The relationship $T_{MODEL-PATIENT}$ between the coordinate system of the model image ($\Sigma_{MODEL}$) and the coordinate system of the patient ($\Sigma_{PATIENT}$) is determined by the EM generator during the above described patient registration process in the conventional manner. Likewise, the relationship $T_{CH-EM}$ between the coordinate system of the chart ($\Sigma_{CHART}$) and the coordinate system of the EM generator ($\Sigma_{EM}$) is also determined according to conventional methods.

Figure 7:
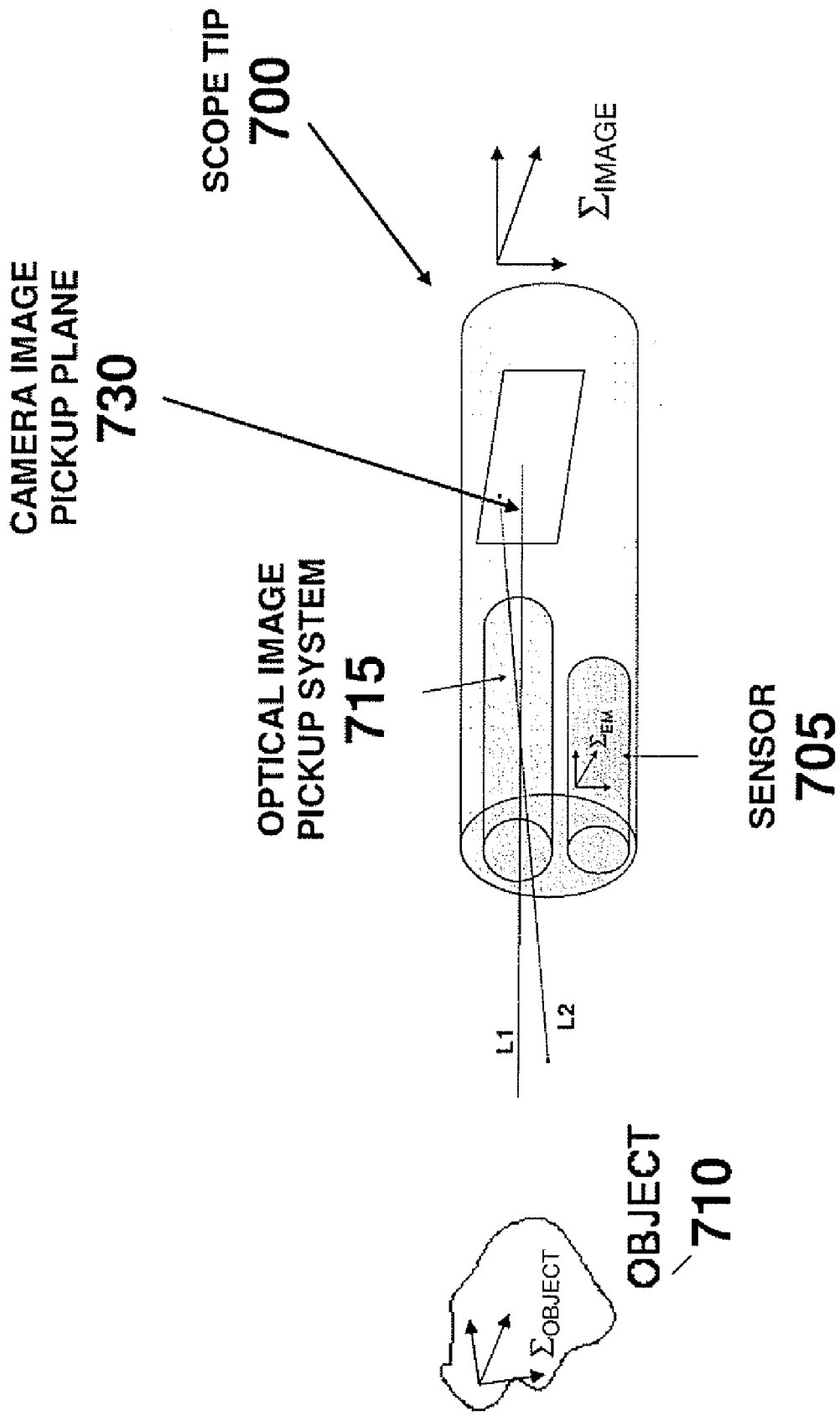
FIG. 7 is a diagram illustrating image pickup of an object according to an aspect of the invention.

Next, referring to FIG. 7, a scope tip 700 is shown to include only an optical image pickup system 715 and a sensor 705, which has the coordinate system $\Sigma_{EM}$, to simplify the following description, but the skilled artisan will readily appreciate that the sensor tip may include any number of sensors, an illumination system, and any other devices, such as, for example, disclosed in U.S. Pat. No. 6,846,286 to Suzuki et al, necessary in carrying out an aspect of the invention without departing from the scope and/or spirit of the invention. An image of an object 710, having a coordinate system $\Sigma_{OBJECT}$, which is the same as $\Sigma_{WORLD}$, and substantially the same as $\Sigma_{EM}$, is projected as L1 and L2 through optical image pickup system 715 and projected onto an image pickup system image pickup plane 730 (described below). The picked up image projection of the object 710 has the coordinate system $\Sigma_{IMAGE}$.

Figure 8:
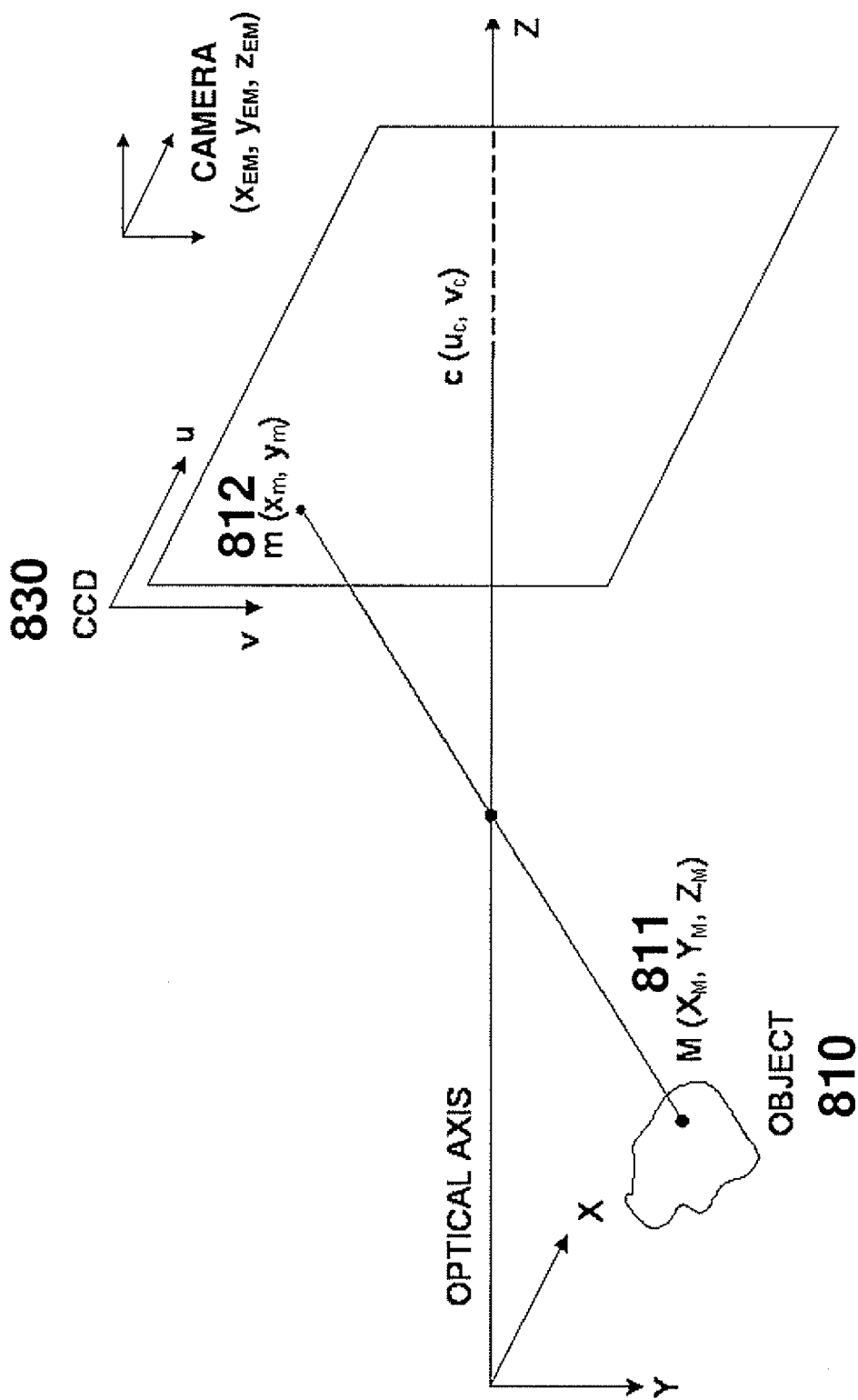
FIG. 8 is an explanatory diagram illustrating projection of an object onto an image pickup device plane.

An implementation of the Tsai calibration method used in determining the calibration matrix $\mathcal{C}^T$ (shown in FIG. 5), including both intrinsic and extrinsic parameters, will next be described according to an aspect of the invention. Referring to FIG. 8, the exemplary scope, which uses, for example, a charge coupled device (CCD) 830 with a two-dimensional image pickup array for an image pickup sensor, has two-dimensional coordinates C ($u_c$, $v_c$), where the z-axis is along the optical axis and the x and y axes are perpendicular to the optical z-axis, as well as perpendicular to each other. A point M 811 of an object 810, which is picked up by the image pickup system CCD 830, has coordinates ($X_M$, $Y_M$, $Z_M$). During image pickup, an image of the object point M is projected through, for example, scope optics onto the CCD 830 and impinges the CCD plane at a point m 812 having coordinates ($x_m$, $y_m$). The scope optics posses a focal length f and a distortion effect. The relationship between the coordinates of the image point m and the coordinates of the object point M may be expressed by the following equations:

$$x_m = X_M f / Z_M \quad (1)$$

$$y_m = Y_M f / Z_M \quad (2)$$

where $x_m$ and $y_m$ are point coordinates of image point m, f is a focal length of the scope optical system positioned between the object and the CCD, and $X_M$, $Y_M$, and $Z_M$ are point coordinates of the object point M. The CCD coordinates (u, v) are defined as follows:

$$u = u_c + x_m / (W_{PIXEL}) \quad (3)$$

$$v = v_c + y_m / (H_{PIXEL}) \quad (4)$$

where $W_{PIXEL}$ is a pixel width, $H_{PIXEL}$ is a pixel height, $u_c$ is the u pixel coordinate at the optical center of the image pickup plane, and $v_c$ is the v pixel coordinate at the optical center of the image pickup plane. Combining equations (1) and (2) with equations (3) and (4), the following equations are attained:

$$Z_M u = Z_M u_c + X_M f / (W_{PIXEL}) \quad (5)$$

$$Z_M v = Z_M v_c + Y_M f / (H_{PIXEL}) \quad (6)$$

As noted above, the calibration matrix $\mathcal{C}^T$ includes both intrinsic and extrinsic parameters. The intrinsic parameters include $u_c$ and $v_c$ noted above, in addition to $\alpha_u$ and $\alpha_v$. The parameters $\alpha_u$ and $\alpha_v$ are defined as follows:

$$\alpha_u = f / (W_{PIXEL}) \quad (7)$$

$$\alpha_v = f / (H_{PIXEL}) \quad (8)$$

The extrinsic parameters include rotational parameters $R_1$, $R_2$, and $R_3$, and translational parameters $t_x$, $t_y$, and $t_z$. The extrinsic parameters pertain to the external orientation of the camera.

Using a linear algorithm to estimate $\mathcal{C}^T$, a linear relationship between the two dimensional image points m (u, v) impinged on the image pickup plane and the three dimensional reference object points M (X, Y, Z) is defined as follows:

$$\begin{bmatrix} su \\ sv \\ s \end{bmatrix} = \begin{bmatrix} q_{11} & q_{12} & q_{13} & q_{14} \\ q_{21} & q_{22} & q_{23} & q_{24} \\ q_{31} & q_{32} & q_{33} & 1 \end{bmatrix} \begin{bmatrix} X \\ Y \\ Z \\ 1 \end{bmatrix} \quad (9)$$

where s is a scalar factor and q is a real number. Accordingly, $q_{34}$ is set equal to 1 where s is set to an arbitrary scale factor. Thus, the above equation (9) can be rewritten as:

$$u = Xq_{11} + Yq_{12} + Zq_{13} + q_{14} - uXq_{31} - uYq_{32} - uZq_{33} \quad (10)$$

$$v = Xq_{21} + Yq_{22} + Zq_{23} + q_{24} - vXq_{31} - vYq_{32} - vZq_{33} \quad (11)$$

However, where the scale factor s has the coordinate value Z, and $\alpha_u$ and $\alpha_v$ are defined as in equations (7) and (8) above, then the image points impinged on the image pickup plane may be derived by applying the endoscope matrix to the coordinates of the object as follows:

$$\begin{bmatrix} su \\ sv \\ s \end{bmatrix} = \begin{bmatrix} \alpha_u & 0 & u_c & 0 \\ 0 & \alpha_v & v_c & 0 \\ 0 & 0 & 1 & 0 \end{bmatrix} \begin{bmatrix} X_M \\ Y_M \\ Z_M \\ 1 \end{bmatrix} \quad (12)$$

Alternatively, equation (12) may be expressed by the following equation:

$$\boldsymbol{a} = \boldsymbol{\mathcal{P}} \cdot \boldsymbol{\mathcal{M}} \quad (13)$$

where $\boldsymbol{a}$ is a homogeneous vector of the image m pixel coordinates, $\boldsymbol{\mathcal{P}}$ is the scope matrix, and z,32 is a homogeneous vector of world coordinates of the object point M. In general, world coordinates will not be specified in a frame whose origin is at the center of the optical system, but will include a translational offset that should be taken into consideration. Thus, taking into consideration extrinsic offset parameters, equation (12) may be modified as follows:

$$\boldsymbol{a} = \boldsymbol{\mathcal{R}} \cdot \boldsymbol{\mathcal{P}} \cdot \boldsymbol{\mathcal{M}} + \boldsymbol{\mathcal{T}} \quad (14)$$

where $\boldsymbol{\mathcal{R}}$ is a rotational matrix component and $\boldsymbol{\mathcal{T}}$ is a translation matrix component of the overall calibration matrix $\mathcal{C}^T$ for transformation between $\Sigma_{EM}$ and $\Sigma_{IMAGE}$ coordinate systems. Since rotation and translation are each performed in the real-world coordinate system (a reference coordinate system having three-dimensions), the resultant transformation will have six degrees of freedom, three degrees of freedom for the rotational part of the transformation $\boldsymbol{\mathcal{R}}$ and three degrees of freedom for the translational part of the transformation $\boldsymbol{\mathcal{T}}$. Thus, the calibration matrix, $\mathcal{C}^T$, including intrinsic and extrinsic parameters, may be expressed as:

$$\mathcal{C}^T = \begin{bmatrix} \alpha_u & 0 & u_c & 0 \\ 0 & \alpha_v & v_c & 0 \\ 0 & 0 & 1 & 0 \end{bmatrix} \begin{bmatrix} R_1 & t_x \\ R_2 & t_y \\ R_3 & t_z \\ 0 & 1 \end{bmatrix} = \begin{bmatrix} \alpha_u R_1 + u_c R_3 + \alpha_u t_x + u_c t_z \\ \alpha_v R_2 + v_c R_3 + \alpha_v t_y + v_c t_z \\ R_3 & t_z \end{bmatrix} \quad (15)$$

where the rotational matrix component $\boldsymbol{\mathcal{R}}$ has vector values $(R_1, R_2, R_3)^T$, and the translational matrix component $\boldsymbol{\mathcal{T}}$ has values $(t_x, t_y, t_z)$.

Accordingly, in determining N number of points on a two dimensional image pickup plane, where N is a positive integer greater than, or equal to 2, from N three dimensional world points and their respective coordinates, the following relationship is attained:

$$\begin{bmatrix} u_1 \\ v_1 \\ u_2 \\ v_2 \\ \vdots \\ u_m \\ v_m \end{bmatrix} = \begin{bmatrix} q_{11} \\ q_{12} \\ q_{13} \\ q_{14} \\ q_{21} \\ \vdots \\ q_{32} \\ q_{33} \end{bmatrix} \quad (16)$$

$$\begin{bmatrix} X & Y & Z & 1 & 0 & 0 & 0 & 0 & -u_1X_1 & -u_1Y_1 & -u_1Z_1 \\ 0 & 0 & 0 & 0 & X_1 & Y_1 & Z_1 & 1 & -v_1X_1 & -v_1Y_1 & -v_1Z_1 \\ \vdots & \vdots & \vdots & \vdots & \vdots & \vdots & \vdots & \vdots & \vdots & \vdots & \vdots \\ X_N & Y_N & Z_N & 1 & 0 & 0 & 0 & 0 & -u_NX_N & -u_NY_N & -u_NZ_1 \\ 0 & 0 & 0 & 0 & X_N & Y_N & Z_N & 1 & -u_NX_N & -u_NY_N & -u_NZ_1 \end{bmatrix}$$

Once the calibration matrix $C^T$ is determined, the relationships amongst the six coordinate systems ($\Sigma_{MODEL}$, $\Sigma_{PATIENT}$, $\Sigma_{EM}$, $\Sigma_{IMAGE}$, $\Sigma_{CHART}$ and $\Sigma_{WORLD}$) displayed in FIG. 5 are determinable, and may be expressed as follows:

$$\Sigma_{IMAGE} = C^T \cdot \Sigma_{CHART} \quad (17)$$

$$\Sigma_{CHART} = T_{EM\text{-}CH} \cdot \Sigma_{EM} \quad (18)$$

$$\Sigma_{EM} = T_{PATIENT\text{-}EM} \cdot \Sigma_{PATIENT} \quad (19)$$

$$\Sigma_{PATIENT} = T_{MODEL\text{-}PATIENT} \cdot \Sigma_{MODEL} \quad (20)$$

$$\Sigma_{IMAGE} = C^T \cdot T_{EM\text{-}CH} \cdot T_{PATIENT\text{-}EM} \cdot T_{MODEL\text{-}PATIENT} \cdot \Sigma_{MODEL} \quad (21)$$

Figure 9:
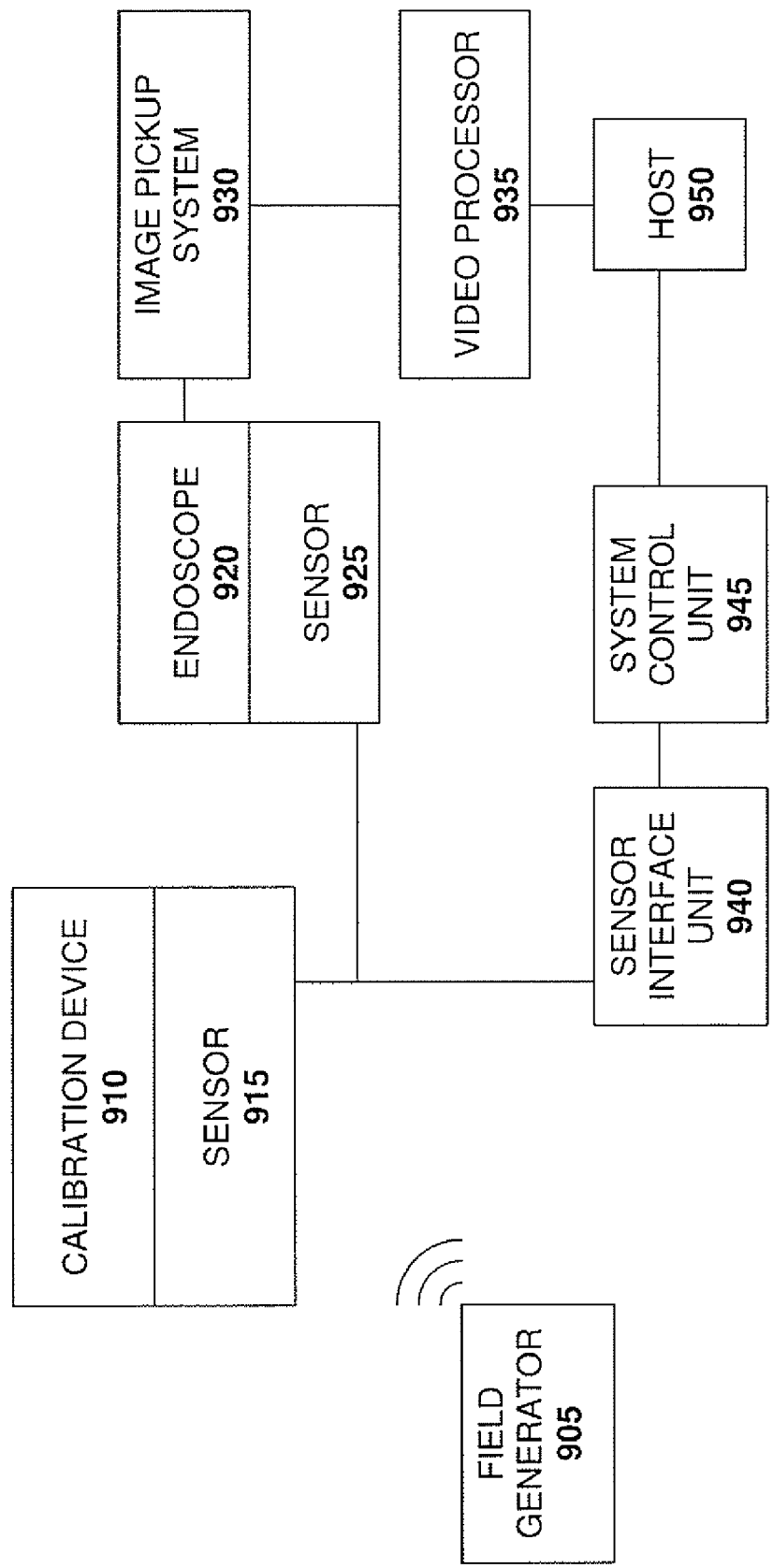
FIG. 9 is an illustration of an embodiment for carrying out an aspect of the invention.

FIG. 9 illustrates an embodiment for performing an augmented reality endoscopic procedure according to an aspect of the invention. According to the exemplary embodiment, a calibration device 910 is provided for calibrating an endoscope device 920, which is connected to an image pickup system 930. A sensor 915 is positioned in the vicinity of the calibration device 910 at some known position in relation to the calibration device. Another sensor 925 is positioned at some other known position in relation to the endoscope device 920. A video processor 935 is connected to the image pickup system 930 and a computer device 950. Sensors 915 and 925 are coupled to a sensor interface unit 940, for example, via a wired connection. Sensor interface unit 940 is coupled through at least one of wired and wireless connections to a system control unit 945. The terminology "at least one of wired and wireless connections" as used in the instant disclosure means one or more wired connection and one or more wireless connections, or any combination thereof, as well as one or more wired connections or one or more wireless connections. The system control unit 945 is coupled to the computer device 950. Although the various devices of exemplary FIG. 9 are described as being interconnected wirelessly, the skilled artisan will recognize that any combination of wired or wireless connection may be made amongst the components, including all wireless, all wired, or any combination thereof. Moreover, the devices may be coupled over a wired or wireless network, such as, for example, a local area network, wide area network, the Internet, or the like.

The calibration device 910 is not limited to the device shown in FIG. 3 and FIG. 5, including a checkerboard pattern with sensors 315a and 315b positioned at diagonal corners of the pattern. Instead, the calibration device 910 may have any pattern suitable for image pickup calibration, and the sensors may be positioned at any position that is capable of providing precise information as to the spatial location of the calibration device, as the skilled artisan will readily appreciate, without departing from the scope and/or spirit of the invention.

For example, as shown in FIGS. 10A-10D, 11A-11B, 12A-12D and 13A-13B the calibration device may have any of a number of non-limiting patterns and sensor arrangements, as described below. The skilled artisan will readily recognize that any color, or color arrangement may be used in the pattern without departing from the scope and/or spirit of the invention. Moreover, any non-limiting pattern, or combination of patterns, may be used, such as, for example, triangles, rectangles, dots, circles, squares, triangles, hexagons, octagons, or any other two-dimensional diagram that lends itself to being generated in a repetitive pattern in a two dimensional plane. Alternatively, or in addition, non-limiting three-dimensional patterns may be used, such as, for example, spheres, cylinders, pyramids, tetrahedrons, boxes, or any other three-dimensional structure that lends itself to generation in a repetitive pattern in three-dimensional space.

The sensors 915 and 925 may be of the same type, or of different types, depending upon the application as the skilled artisan will readily recognize, without departing from the scope and/or spirit of the invention. For example, both sensors 915 and 925 may be miniature sensor coils that may be incorporated into medical instruments, such as, for example, the endoscope 920 and/or the calibration device 910. The sensors may provide five degrees of freedom (5 DOF), or they may provide six degrees of freedom (6 DOF) depending on the intended application. For example, two sensors may be affixed to the scope in an orthogonal configuration for five degrees of freedom. Alternatively, a single sensor may be provided in the scope for six degrees of freedom.

The sensors may be incorporated into the instruments, affixed to the instruments, or positioned at some remote physical location that varies in accordance with movement of the instruments. The sensor 925, for example, may be affixed to, or integrated into the endoscope device 920 as shown, for example, in FIG. 6. Alternatively, sensor 925 may be externally affixed to the endoscope device 920 (not shown) or inserted into a channel in the endoscope device. Moreover, the endoscope device 920 end may be configured from one or more cylindrical casings or rings that are made from continuous or discrete variable electromagentic response segments such that the electromagnetic response of each segment varies as a function of its location along the perimeter of the cylindrical casing or ring, thereby providing accurate translational and rotational spatial position detection.

Further, the sensor 925, for example, may be provided integral to the calibration device 910 as shown in FIG. 5, or it may be affixed to a support that movably supports the calibration device 910 (not shown) at some fixed spatial relationship For example, sensor 925 may be affixed to a calibration device 910 that may be configured from a water-resistant chart, or laminated in a predetermined position on a printed chart that may be also laminated. Alternatively, the calibration device 910 and the sensor 925 may be affixed to the field generator 905. The skilled artisan will appreciate that the term "affix" as used in the instant disclosure includes to attach by some adhesive, or through a coupling mechanism, or the like, in a temporary or permanent manner. Moreover, the term "fixed" is herein used to describe a non-varying relationship between two or more objects, two or more points, or any combination of objects and points, where the relationship may be temporary or permanent by nature. For example, the relationship may be temporary such as in the instance of maintaining a non-varying spatial relationship between the calibration device 910 and sensor 925 during the exemplary non-limiting medical procedure disclosed herein.

The sensors 915 and 925 react, for example, to an electromagnetic field generated by field generator 905 and provide spatial location data of their positions in three-dimensional coordinates. The positional data is received by the sensor interface unit 940. The sensor interface unit 940, which provides increased distance between the sensors 915 and 925 and the system control unit 945 while minimizing the potential for noise, transmits sensor position data to the system control unit 945. The system control unit 945 receives the sensor position data from the sensor interface unit 940 and calculates positions and orientations of the sensors based on the received data. The system control unit 945 communicates with the host device 950. The host device 950 may be a personal computer, such as, for example, a desktop workstation, a laptop computer, a notebook computer, an array of processors, a network of computers, or any other device capable of processing the necessary algorithms for image pickup calibration and display of the necessary information to the user without departing from the scope and/or spirit of the invention.

The skilled artisan will recognize that infrared (IR) transmitters may be used instead of, or in addition to EM sensors for sensors 915 and 925. This may be a desirable embodiment according to an aspect of the invention, for example, where the area to be explored is buried or surrounded by metallic objects. By way of non-limiting example, in searching and locating victims of natural disasters such as, for example, earthquakes, where the victim may be buried under metallic debris, an EM sensor may not be as effective as an IR transmitter and so it may be desirable to instead use IR transmitters. In the IR transmitter-based non-limiting example, the field generator 905 is not needed and the sensor interface unit 940 will be configured to respond to IR signals generated by the IR transmitters. The skilled artisan will recognize that any type of mechanism that facilitates accurate spatial tracking may be used for the sensors 915 and 925 without departing from the scope and/or spirit of the invention.

The host device 950 communicates with the system control unit 945 and receives calculated position and orientation information from the system control unit 945. The host device 950 performs the above discussed coordinate system transformations, determining the coordinate systems, $\Sigma_{MODEL}$, $\Sigma_{PATIENT}$, $\Sigma_{EM}$, $\Sigma_{IMAGE}$, $\Sigma_{CHART}$ and $\Sigma_{WORLD}$, as well as the transformation relationships amongst the different coordinate systems. The host device 950 corrects for intrinsic and extrinsic errors, for example, as discussed above, and performs the necessary transformations between the coordinate systems in order to facilitate accurate navigation of the equipment used for the procedure, such as, for example, a endoscope. The host device 950 causes the model image 305*a*, the corrected two dimensional image 305*b* picked up by the image pickup system, the image map 305*c*, and the graphic user interface display area 305*d* (FIG. 3) to be displayed.

The endoscope device 920 may be, for example, of the type described in U.S. Pat. No. 6,846,286, incorporated herein by reference in its entirety. The image pickup system of the endoscope is calibrated by positioning the endoscope relative to the calibration device 910 in such a manner that one or more images are recorded by the image pickup system 930. The recorded images are used to calibrate the endoscope device as discussed above. A video signal generated by the image pickup system 930 is transmitted to the video processor 935. The video processor 935 receives the video signal from video camera 930 and perform processes such as, for example, image signal enhancement, edge enhancement, black current reduction, hue adjustment, white balancing, and the like, and transmits a processed video signal to host device 950. Video processor 935 may perform calibration of the image pickup system 930, for example, through calculating the relationships of the coordinate systems and correcting the video signal output from image pickup system 930, for example, by performing the Tsai method on a MATLAB® toolbox, as described above.

Although the endoscope device 920 has been described above as having a single image pickup device, the endoscope device 920 may include multiple image pickup devices. For example, two image pickup devices may be used in the endoscope device 920 to provide stereoscopic image pickup. In that instance, the calibration and correction described herein would be performed individually for each image pickup device as described above.

Alternatively, the image pickup system calibration and correction may be performed on the host 950. As discussed above, software for use with image processing software on host 950, such as, for example, MATLAB®, is available. The image pickup system calibration and image processing software may be installed on a general processing computer, to calibrate and correct a scope prior to its actual application in surgical and/or diagnostic procedures. Typically, a checkered-board pattern, which is placed on a flat surface, is used to calibrate the camera. Depending on the type of procedure that is to be performed, the calibration process may take into consideration the effect of liquid or gas that the scope is anticipated to encounter during the intended procedure since a focal length may vary depending on the type of medium in which the scope will be immersed.

Although FIGS. 10A-10D and 11A-11B are shown as having two sensor 915A and 915B, and FIGS. 12A-12D and 13A-13B are shown as having a single sensor 915, any number of sensors may be used as the skilled artisan will deem appropriate without departing from the scope and/or spirit of the invention. Moreover, the sensors, for example, may be arranged anywhere on the calibration device, or at some fixed remote location in relation to the calibration device as long as the sensors are able to convey the precise location of the calibration device in three dimensional coordinates with respect to the world coordinate system.

Figure 10B:
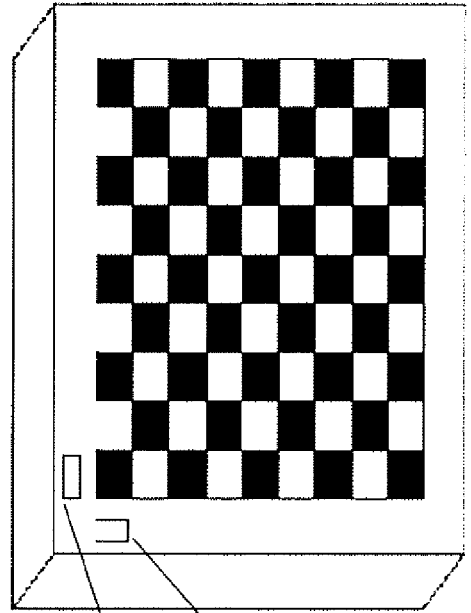
FIGS. 10A-10D are illustrations of examples of calibration devices with two sensors that may be used according to an aspect of the invention.
Figure 10D:
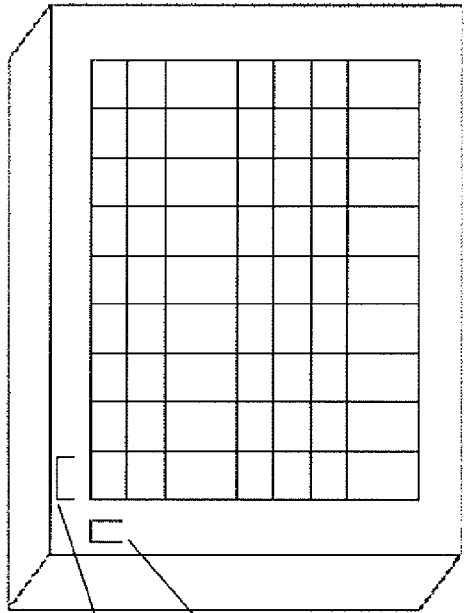
Figure 10A:
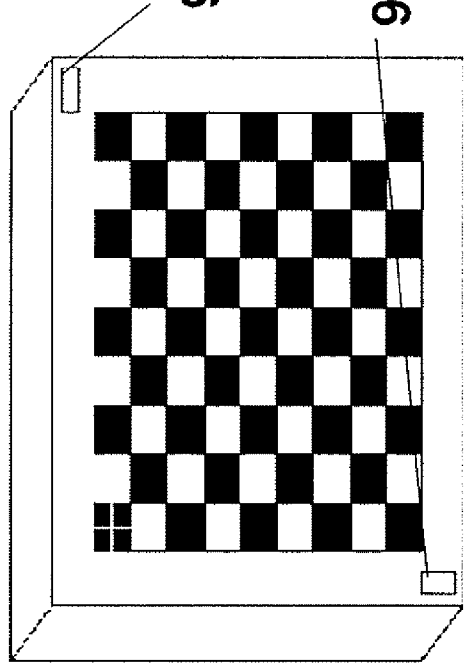

FIG. 10A shows a calibration device according to an embodiment of the invention having a checkerboard, black and white pattern with two sensors positioned at diagonal ends of the calibration device. One sensor is positioned in the right-topmost corner along the horizontal axis, and the other is positioned in the left-lowermost corner along the vertical axis.

FIG. 10B shows a calibration device according to an embodiment of the invention having a checkerboard, black and white pattern with two sensors positioned adjacent to each other at one corner of the calibration device. The exemplary sensors are positioned in the left-topmost corner of the calibration device. One sensor is positioned along the horizontal axis of the calibration device, and the other is positioned along the vertical axis of the calibration device.

Figure 10C:
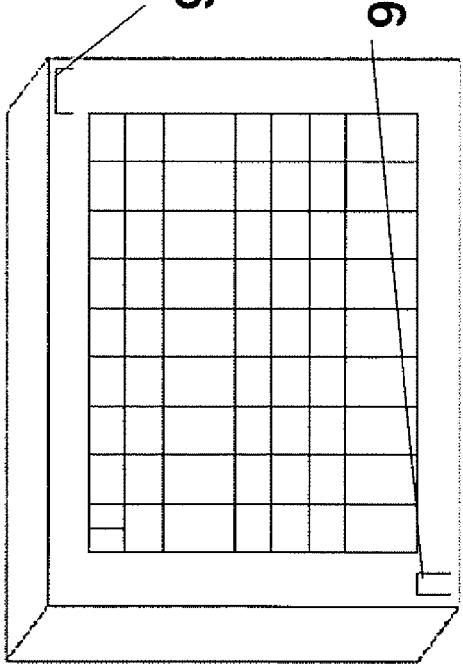

FIG. 10C shows a calibration device according to an embodiment of the invention having a grid pattern with two sensors positioned at diagonal ends of the calibration device. One sensor is positioned in the right-topmost corner along the horizontal axis, and the other is positioned in the left-lowermost corner along the vertical axis.

FIG. 10D shows a calibration device according to an embodiment of the invention having a grid pattern with two sensors positioned adjacent to each other at one corner of the calibration device. The exemplary sensors are positioned in the left-topmost corner of the calibration device. One sensor is positioned along the horizontal axis of the calibration device, and the other is positioned along the vertical axis of the calibration device.

FIG. 11A shows a calibration device according to an embodiment of the invention having a dot pattern with two sensors positioned at diagonal ends of the calibration device. One sensor is positioned in the right-topmost corner and the other is positioned in the left-lowermost corner.

FIG. 11B shows a calibration device according to an embodiment of the invention having a dot pattern with two sensors positioned adjacent to each other at one corner of the calibration device. The exemplary sensors are positioned in the left-topmost corner of the calibration device. One sensor is positioned along the upper-horizontal axis of the calibration device, and the other is positioned along the left-vertical axis of the calibration device.

FIG. 12A shows a calibration device according to an embodiment of the invention having a checkerboard, black and white pattern with a single sensor positioned at a corner end of the calibration device. The sensor is positioned in the right-topmost corner along the horizontal axis.

FIG. 12B shows a calibration device according to an embodiment of the invention having a checkerboard, black and white pattern with a sensor positioned at one corner of the calibration device. The exemplary sensor is positioned in the left-topmost corner of the calibration device along the horizontal axis of the calibration device.

FIG. 12C shows a calibration device according to an embodiment of the invention having a grid pattern with two sensors positioned at diagonal ends of the calibration device. One sensor is positioned in the right-topmost corner and the other is positioned in the left-lowermost corner.

FIG. 12D shows a calibration device according to an embodiment of the invention having a grid pattern with a single sensor positioned at one corner of the calibration device. The exemplary sensor is positioned in the left-topmost corner of the calibration device, along the horizontal axis of the calibration device.

FIG. 13A shows a calibration device according to an embodiment of the invention having a dot pattern with a single sensor positioned at a corner of the calibration device. The sensor is positioned in the right-topmost corner along the horizontal axis.

FIG. 13B shows a calibration device according to an embodiment of the invention having a dot pattern with a single sensor positioned at one corner of the calibration device. The exemplary sensor is positioned in the left-topmost corner of the calibration device along the vertical axis of the calibration device.

Figure 14:
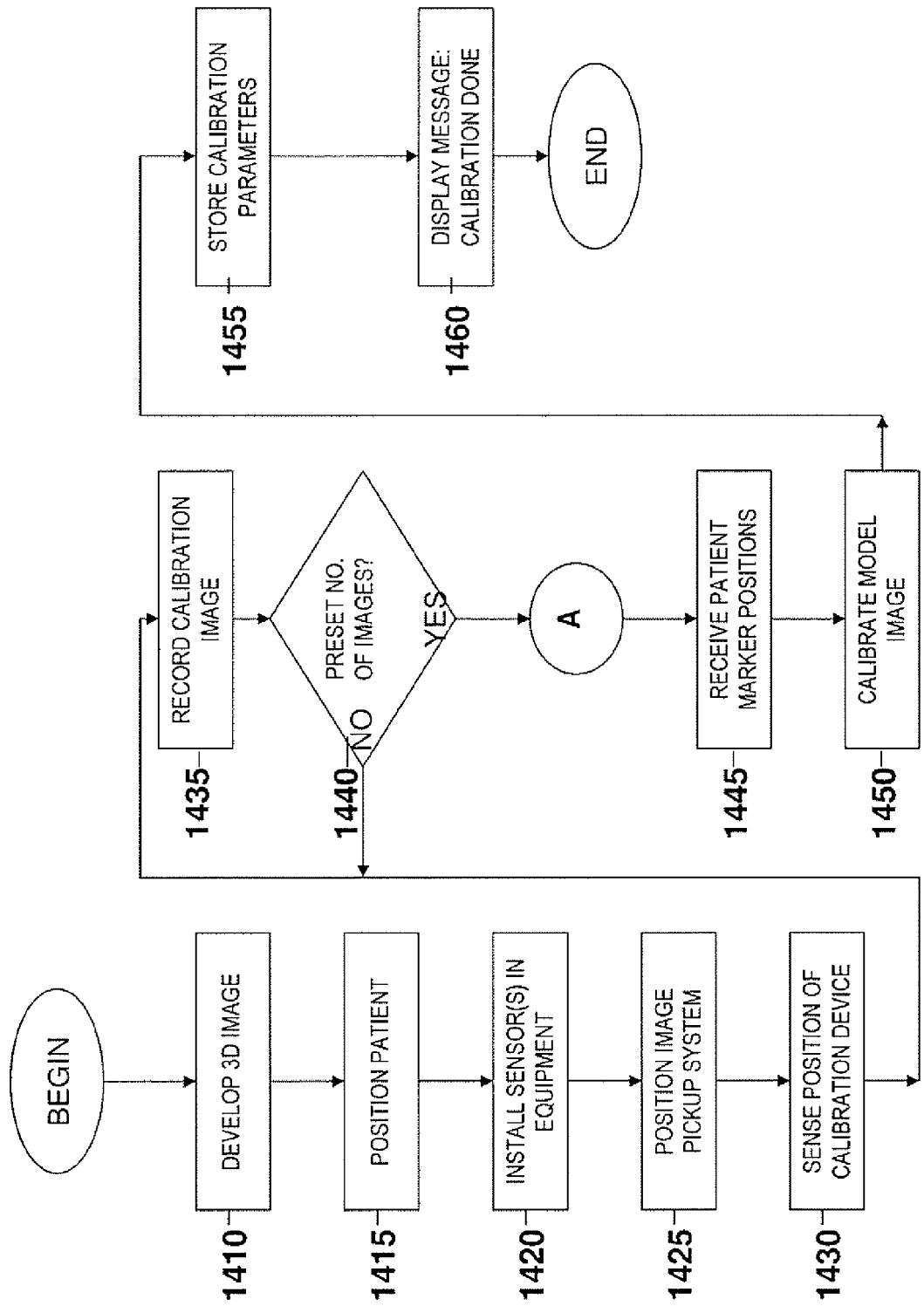
FIG. 14 is an embodiment of a process for performing endoscopic navigation according to an aspect of the invention.

Referring to FIG. 14, an exemplary process according to an aspect of the invention will now be described. The process may be performed, for example, by the host 950, or another device capable of carrying out the process as the skilled artisan will readily appreciate, without departing from the scope and/or spirit of the invention. Upon initialization, three-dimensional model image information, such as, for example a preprocedure CT scan or MRI image, including three dimensional coordinate information, is loaded or transferred, directly or indirectly to host device 950. At step 1410 the model image information is processed and displayed in a manner perceivable by the user.

At step 1415 a patient is positioned in a manner commensurate with the type of procedure the patient is expected to undergo. Depending on the type of patient registration system employed, sensors may be affixed to the patient in an area of the patient that is to undergo the procedure. The placement of the patient registration sensors may be performed at step 1415. In the process illustrated in FIG. 14 by way of non-limiting example, the patient registration method employed will be a patient touch registration method as described below.

At step 1420 sensors are affixed, or inserted into a penetrating device that is to be used for the procedure. Two sensors may be orthogonally positioned to provide five-degrees-of-freedom (5 DOF), or a single sensor may be positioned to provide six-degrees-of-freedom (6 DOF). Moreover, at least one sensor is affixed to a calibration device if such is not already provided in the calibration device. In the non-limiting example disclosed herein, the penetrating device is a flexible endoscope, and two sensors are inserted through, for example, instrument channels of the endoscope tip. However, the skilled artisan will readily appreciate that the penetrating device may be a rigid endoscope, a catheter, a cannula, or any other device that may be inserted into an object and navigated in the object. Similarly, the calibration device is disclosed as including one or two position sensors affixed to the device. However, the skilled artisan will readily recognize that any number of sensors may be inserted into the calibration device, affixed to the calibration device, or affixed to some mechanism that remains in fixed relation to the calibration device, without departing from the scope and/or spirit of the invention. The process proceeds to step 1425.

At step 1425, the exemplary flexible endoscope tip, including an image pickup system, is positioned so that the calibration device is within the image pick up field of the image pickup system. At step 1430, which may, instead, be performed before, or simultaneously with step 1425, or after step 1435, position information is determined for the sensors, for example, inserted in the flexible endoscope tip. At step 1435, the image pickup system is caused to capture an image of the calibration device. Although it is preferable that a plurality of images (such as, for example, five or more), of the calibration device be captured by the image pickup device, any number of images may be used as the skilled artisan will deem appropriate, without departing from the scope and/or spirit of the invention. At step 1440, a determination is made whether a preset, or predetermined number of images have been recorded by the image pickup system. Typically, the preset number of images may be set to five or more images, but the number will vary as a function of the procedure to be performed, the user's preference, the scale of the procedure and/or scope, and the like, as the skilled artisan will appreciate. If the preset number of images of the calibration device have been recorded ("YES" at step 1440), the process will proceed to a process A illustrated in FIG. 15, and continue to step 1445 upon completion of the process A. However, if the preset number of images has not been recorded ("NO" at step 1440), the user will be instructed, for example, by way of display or sound message to repeat image capture.

Figure 15:
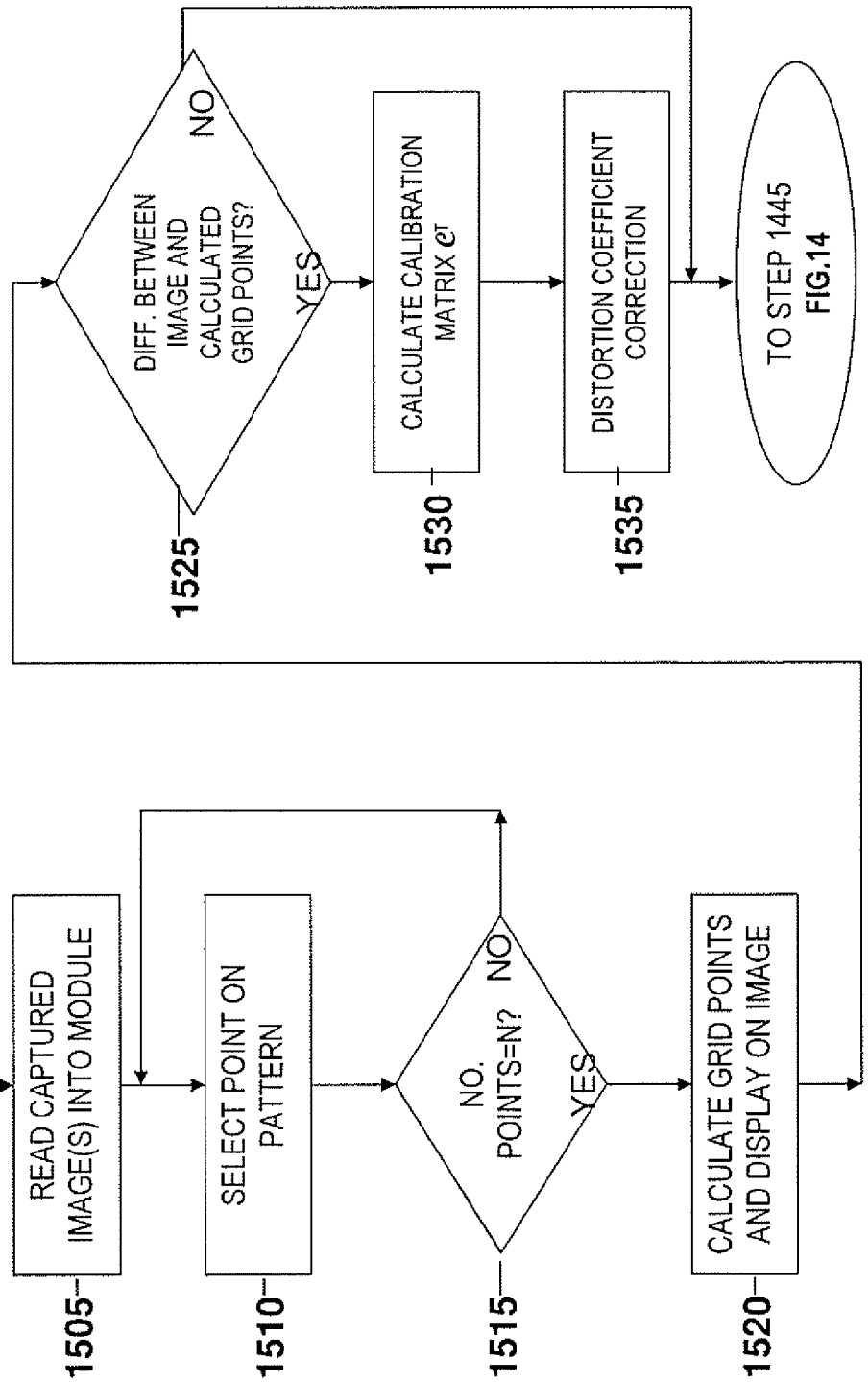
FIG. 15 is an embodiment of a process correcting distortion according to an aspect of the invention.
Figure 16B:
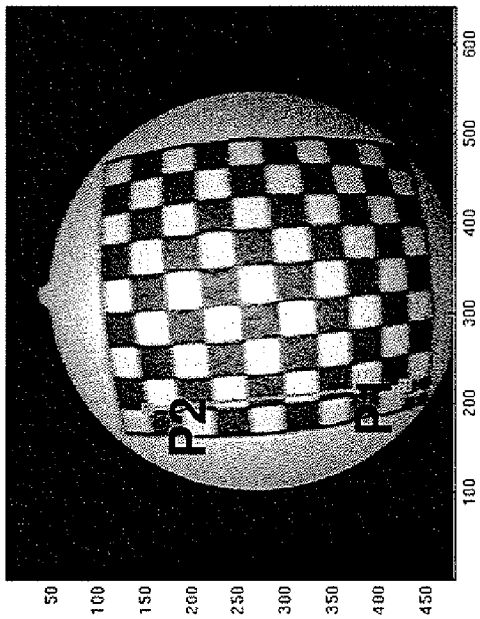
FIGS. 16A-16D are examples of grid point selection on a captured image of a calibration device according to an aspect of the invention.
Figure 16D:
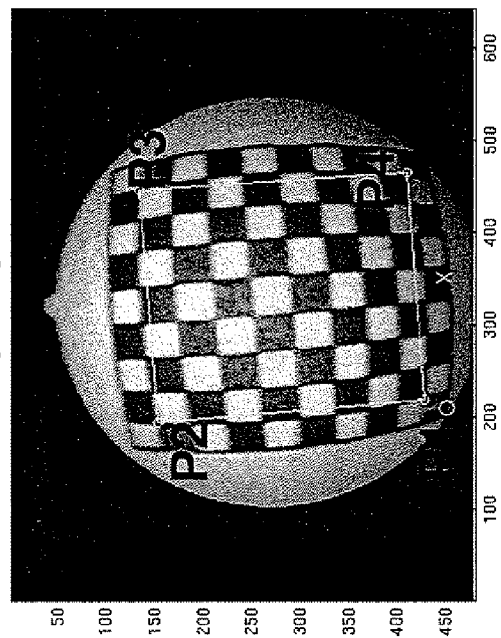
Figure 16A:
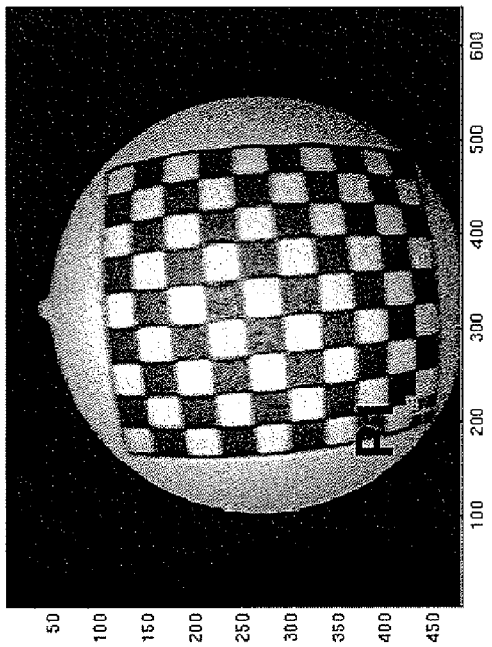

Referring to FIG. 15, after the preset number of images of the calibration device are recorded, or captured by the image pickup system, the captured images are read into an image capture module at step 1505. At step 1510, points are selected on the captured image(s). For illustration purposes only, a non-limiting example is provided where the number of selection points, N is equal to four, however, the number of selection points may be any appropriate number as the skilled artisan will readily recognize. Referring to FIG. 16A, a first point P1, located on a bottom-left most area of a captured image of a checkerboard pattern is selected at step 1510. The first point P1 is designated the origin, and the next three points will be selected going clockwise in FIGS. 16B-16D.

Figure 16C:
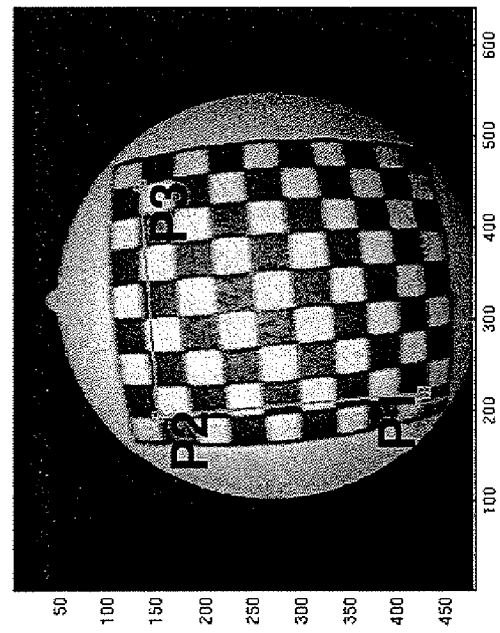

The process proceeds to step 1515 where a determination is made that four points have not yet been selected ("NO" at step 1515). Step 1510 is repeated and a point P2, located in the left-top most corner of the checkerboard pattern, as shown in FIG. 16B is selected. Then, a third point is selected in step 1510 at point P3, located in the right-top most corner of the checkerboard pattern, as shown in FIG. 16C. Step 1510 is performed a fourth time and a fourth point P4, located in the right-bottom most corner of the checkerboard pattern, as shown in FIG. 16D is selected. Once the number of points equals the number of preset points in step 1515 ("YES" at step 1515), the process proceeds to step 1520. Although the points were designated in the non-limiting example above in a clockwise fashion, the points could equally be designated in a counterclockwise fashion, or in any other manner deemed appropriate by the skilled artisan in selecting at least one point for calibration.

Figure 17A:
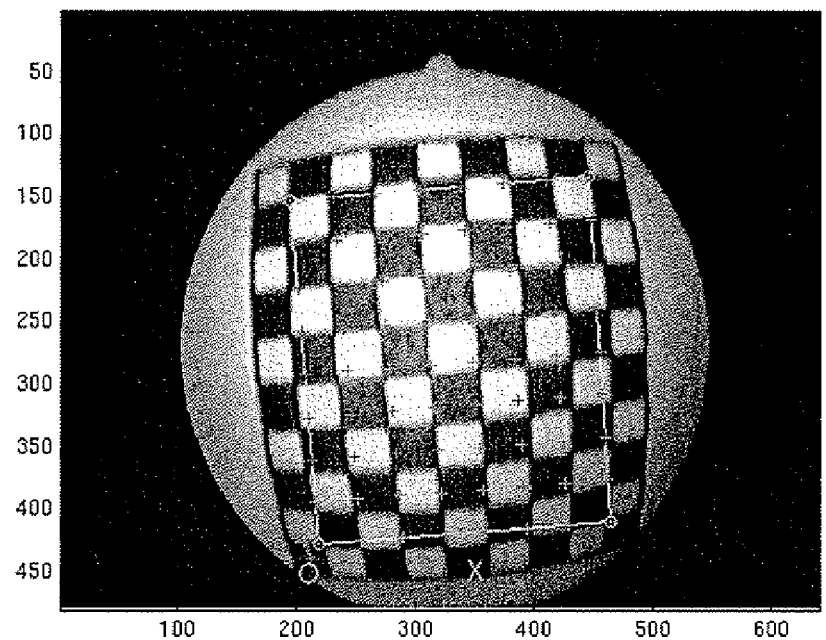
FIGS. 17A is an illustrative example where calculated grid points may cause distortion according to an aspect of the invention.

At step 1520, an array of grid points is calculated based on a predetermined distance and the number of grids on the calibration device, and the grid points are displayed superimposed on the captured image as shown in FIG. 17A. A determination is then made at step 1525 whether a difference exists between the calculated grid points and the underlying captured image by comparing the difference between values for the calculated grid points and values for the underlying captured image and calculating a difference value. The difference value is then compared to a predetermined threshold value, and if the difference value is equal to or above the threshold value, a difference is determined to exist. However, if the difference value is below the threshold value, then a difference is determined not exist. Accordingly, if no difference exists ("NO" at step 1525), the process proceeds to step 1445 in FIG. 14. But, if a difference is determined to exist between the calculated grid points and the underlying captured image, then the process proceeds to step 1530.

Figure 17B:
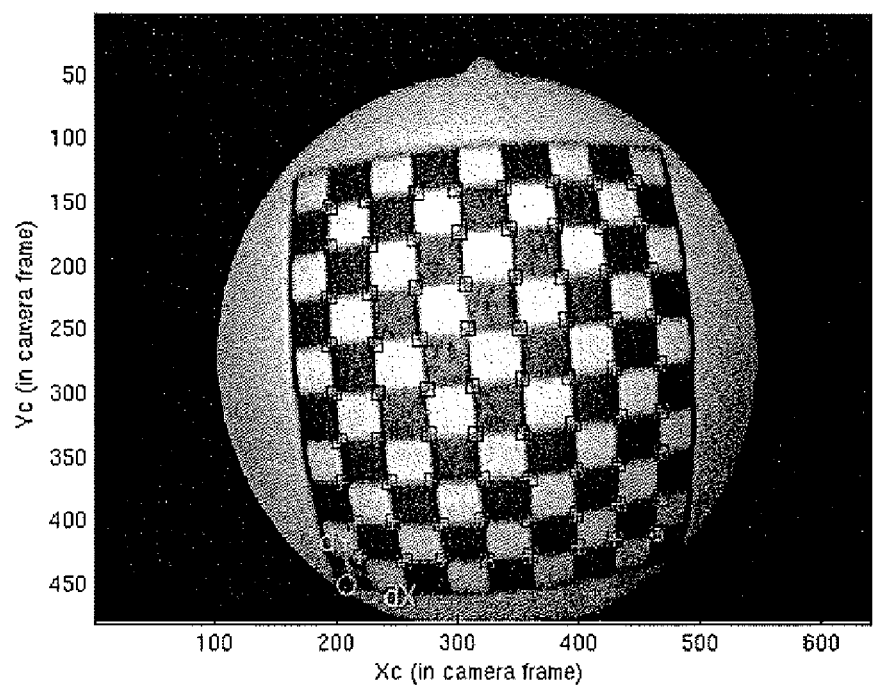
FIG. 17B is an illustrative example where distortion correction has been performed according to an aspect of the invention.

At step 1530, a calibration matrix $\mathcal{C}^T$ is calculated as discussed above, and the process progresses to step 1535. At step 1535 the captured image from the image pickup system is corrected using the distortion coefficients of the calibration matrix $\mathcal{C}^T$ to cause, for example, an image as shown in FIG. 17B to be reproduced and displayed. As shown in FIG. 17B, the grid points are shown after distortion coefficient correction as superimposed on the captured image. Upon completion of the correction step 1530, the process proceeds to step 1445 in FIG. 14.

At step 1445, position information is received for the patient. By way of non-limiting example, as described above, position information for each of a plurality of points on an area that is to undergo the procedure, or within close proximity to the area, may be registered by the user briefly touching a conical skin fiducial at each point. Once all of the patient position information points have been registered and received at step 1445, the process proceeds to step 1450. At step 1450 the model image is calibrated to the patient position information and the process proceeds to step 1455. At step 1455, the calibration parameters for the calibration matrix $\mathcal{C}^T$ are stored, and a message is displayed at step 1460 that calibration has been completed and that the penetration device is ready for implementation.

According to another aspect of the invention, code, including distinct code segments, is provided on at least one computer readable medium for carrying out, for example, the non-limiting processes shown in FIG. 14 and FIG. 15. The code, including code segments may be transferred from the at least one computer readable medium, directly or indirectly, for example, to host device 950. Alternatively, the code, including code segments may be transmitted directly or indirectly, for example, to the host device 950 via wired or wireless communication. The computer readable medium may include code segments for causing a computer device to perform each of the steps of the processes illustrated in FIG. 14 and FIG. 15. For example, the non-limiting computer readable medium may include a three-dimensional image development code segment that causes the computer device to receive a preprocedure image, such as, for example, a CT scan or MRI image, or the like, and develop a model image.

A patient positioning code segment may be provided to cause a patient support mechanism, such as, for example, an operating table, or the like, to be automatically positioned for an intended procedure. Alternatively, the patient positioning code segment may cause a display of a message specifying, for example, how a patient should best be positioned for the intended procedure.

A sensor install code segment may be provided to cause an automated device, such as, for example, a robotic device, to install or affix sensors to a penetrating device. Alternatively, the sensor install code segment may cause a computer device provide instructions via, for example, a graphic user interface, to a user instructing the user of best locations to install or affix sensors on the penetrating device and/or the patient based on the intended procedure, the type of equipment used, the user's skill level, and the like.

A position image pickup system code segment may be provided to cause a computer controlled image pickup system support mechanism to be positioned so that a calibration device is in the field of image pickup of the image pickup system. Alternatively, the position image pickup system code segment may cause a computer device to provide instructions, via, for example, to a user instructing the user of a best location to position the penetrating device so that it may be properly calibrated. The instructions may include, for example, voice or display commands, instructing the user to move the penetrating device up, down, left, right, away, near, pitch up, pitch down, pitch right, pitch left, rotate clockwise, and/or rotate counterclockwise based on the intended procedure, the type of equipment used, the user's skill level, and the like, as the skilled artisan will readily appreciate without departing from the scope and/or spirit of the invention.

A sense position of calibration device code segment may be provided to cause a computer device to determine a spatial position of one or more calibration devices. The sense position of calibration device code segment may provide three dimensional coordinates for the calibration device.

A record calibration image code segment may be provided to cause the image pickup system of the penetrating device to capture or record an image of the calibration device, or to cause a computer device to instruct the image pickup system to capture or record the image.

A number of images determination code segment may be provided to cause a computer device to determine whether a preset number of images are captured by the image pickup system.

A captured image read code segment may be provided to cause a computer device to read captured images into a captured image processing module.

A point selection code segment may be provided to cause a computer device to select points on a calibration device. A number of points determination code segment may be provided to cause a computer device to determine whether a selected number of points have been selected on the calibration device.

A grid point calculation code segment may be provided to cause a computer device to calculate at least one grid point on a calibration device and to cause the grid points to be displayed as superimposed points on an image of the calibration device.

A grid point difference determination code segment may be provided to cause a computer device to determine whether a difference above a predetermined threshold exists between the grid points and the image of the calibration device.

A calibration matrix calculation code segment may be provided to cause a computer device to calculate a calibration matrix for a particular penetrating device. A distortion coefficient correcting code segment may be provided to cause a computer device to correct for intrinsic and/or extrinsic manifestations of the penetrating device.

A patient position information receiving code segment may be provided to cause a computer device to receive patient position information so as to accurately determine a patient's position in, for example, three dimensions.

A calibration parameter storing code segment may be provided to cause a computer device to store calibration parameters. And, a calibration done display code segment may be provided to cause a computer device to display a message to the user that calibration has been completed.

Although the present specification describes components and functions that may be implemented in particular embodiments with reference to particular standards and protocols, the invention is not limited to such standards and protocols. Each of the standards, protocols and languages represent examples of the state of the art. Such standards are periodically superseded by faster or more efficient equivalents having essentially the same functions. Accordingly, replacement standards and protocols having the same or similar functions are considered equivalents thereof.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope and spirit of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments that fall within the true spirit and scope of the present disclosure. Thus, to the maximum extent allowed by law, the scope of the invention is to be determined by the broadest permissible interpretation of the following claims and their equivalents, and shall not be restricted or limited by the foregoing detailed description.

Although several exemplary embodiments have been described, it is understood that the words that have been used are words of description and illustration, rather than words of limitations Changes may be made within the purview of the appended claims, as presently stated and as amended, without departing from the scope and spirit of the invention in its aspects. Although the description refers to particular means, materials and embodiments, the invention is not intended to be limited to the particulars disclosed, but rather extends to all functionally equivalent structures, methods, and uses such as are within the scope of the appended claims.

What is claimed:

1. A scope navigation apparatus comprising:
   a scope configured to be inserted into an object, the scope including at least one sensor;
   a calibration device configured to calibrate the scope;
   a calibration device sensor positioned in a fixed position in relation to the calibration device;
   an image pickup device that records at least one image, the at least one image being an image of the calibration device;
   an axis determiner that determines an optical axis of the image pickup device, a central axis of the at least one sensor being offset from the optical axis of the image pickup device;
   a location determiner that senses a location of the at least one sensor and a location of the calibration device sensor; and
   a processor that corrects the at least one image recorded by the image pickup device based upon the location of the at least one sensor and the location of the calibration device sensor, said processor being configured to compensate for the offset between the central axis of the at least one sensor and the optical axis of the image pickup device.

2. The apparatus according to claim 1, the processor comprising:
   a video processor; and
   a host device, where at least one of the video processor and host device corrects the at least one image recorded by the image pickup device.

3. The apparatus according to claim 1, the location determiner comprising:
  a sensor interface unit; and
  a system control unit, wherein the sensor interface unit senses the location of the at least one sensor and the location of the calibration device sensor.

4. The apparatus according to claim 1, further comprising a field generator that generates an electromagnetic field, wherein said location determiner senses the location of the at least one sensor and the location of the calibration device sensor based on the electromagnetic field.

5. The apparatus according to claim 4, wherein the calibration device is positioned in a fixed relation to the field generator.

6. The apparatus according to claim 1, wherein the at least one sensor is inserted into a channel of the scope, and said calibration device sensor is affixed to the calibration device.

7. The apparatus according to claim 1, wherein the calibration device is at least one of a checkerboard pattern, a dot pattern, or a grid pattern.

8. A method for calibrating and correcting an image to be displayed, the method comprising:
  recording an image of a calibration device, the calibration device located in a fixed position in relation to at least one calibration device sensor;
  determining an optical axis of an image pickup device, the image pickup device including at least one sensor;
  detecting a location of the at the least one calibration device sensor and a location of the at least one sensor;
  determining a parameter value for calibrating the image pickup device;
  compensating an offset between a central axis of the at least one sensor and the optical axis; and
  calibrating the recorded image based on the parameter value.

9. The method according to claim 8, said determining a parameter value comprising:
  selecting a first point on the recorded image;
  calculating a first determination point based on the selected first point;
  determining a difference value between the selected point and the first determination point; and
  comparing the difference value with a threshold value.

10. The method according to claim 9, further comprising:
  determining the difference value to be greater than, or equal to the threshold value; and
  calculating a calibration matrix for calibrating the image pickup device.

11. The method according to claim 10, wherein the calibration matrix includes at least one intrinsic parameter and at least one extrinsic parameter.

12. The method according to claim 11, the calibration matrix being based on a relationship between a three dimensional coordinate system of the calibration device and a two dimensional coordinate system of the image pickup device.

13. The method according to claim 9, wherein said calibrating is based on at least one of five degrees of freedom and six degrees of freedom.

14. The method according to claim 9, further comprising:
  setting the first point as an origin point; and
  selecting a second point in at least one of a clockwise and counterclockwise direction.

15. The method for calibrating according to claim 8, further comprising providing at least one of a checkerboard pattern, a dot pattern, or a grid pattern, as the calibration device.

16. A computer readable medium comprising:
  an image recording code segment that causes recording an image of a calibration device, the calibration device located in a fixed position in relation to at least one calibration device sensor;
  a determining code segment that causes determining an optical axis of an image pickup device, the image pickup device including at least one sensor;
  a detecting code segment that causes detecting a location of the at least one sensor and a location of the at least one calibration device sensor;
  a parameter determining code segment that causes determining a parameter value for calibrating the image pickup device;
  a compensating code segment that causes compensating an offset between a central axis of the at least one sensor and the optical axis of the image pickup device; and
  a calibrating code segment that causes calibrating the image pickup device based on the parameter value.

17. The computer readable medium according to claim 16, the determining code segment comprising:
  a point selecting code segment that causes selecting a first point on the recorded image;
  a determination point calculating code segment that causes calculating a first determination point based on the selected first point;
  a difference value determining code segment that causes determining a value between the selected point and the first determination point; and
  a difference value comparing code segment that causes comparing the difference value with a threshold value.

18. The computer readable medium according to claim 16, further comprising:
  a difference value determining code segment that causes determining the difference value to be greater than, or equal to the threshold value; and
  a calibration matrix code segment that causes calculating a calibration matrix for calibrating the image pickup device.

19. The computer readable medium according to claim 18, wherein the calibrating is based on at least one of five degrees of freedom and six degrees of freedom, and wherein the calibration matrix includes at least one intrinsic parameter and at least one extrinsic parameter.

20. The computer readable medium according to claim 18, the calibration matrix being based on a relationship between a three dimensional coordinate system of the calibration device and a two dimensional coordinate system of the image pickup device.

* * * * *